United States Patent
Gassler et al.

(10) Patent No.: US 11,559,387 B2
(45) Date of Patent: Jan. 24, 2023

(54) SUBSTRATE WITH ROTATABLE STRUTS FOR MEDICAL DEVICE

(71) Applicant: W. L. Gore & Associates, Inc., Newark, DE (US)

(72) Inventors: Paul D. Gassler, Lincoln University, PA (US); Nathan L. Friedman, Flagstaff, AZ (US); Bruce M. Steinhaus, Flagstaff, AZ (US); Edward H. Cully, Newark, DE (US); Jeffrey B. Duncan, Flagstaff, AZ (US)

(73) Assignee: W. L Gore & Associates, Inc., Newark, DE (US)

( * ) Notice: Subject to any disclaimer, the term of this patent is extended or adjusted under 35 U.S.C. 154(b) by 72 days.

(21) Appl. No.: 16/647,204

(22) PCT Filed: Sep. 7, 2018

(86) PCT No.: PCT/US2018/049983
§ 371 (c)(1),
(2) Date: Mar. 13, 2020

(87) PCT Pub. No.: WO2019/055311
PCT Pub. Date: Mar. 21, 2019

(65) Prior Publication Data
US 2020/0214825 A1 Jul. 9, 2020

Related U.S. Application Data

(60) Provisional application No. 62/557,488, filed on Sep. 12, 2017.

(51) Int. Cl.
*A61F 2/07* (2013.01)
*A61F 2/95* (2013.01)
*A61M 37/00* (2006.01)

(52) U.S. Cl.
CPC .............. *A61F 2/07* (2013.01); *A61F 2/95* (2013.01); *A61F 2220/0016* (2013.01);
(Continued)

(58) Field of Classification Search
CPC ...... A61F 2/07; A61F 2/95; A61F 2220/0016; A61F 2250/0067; A61F 2/958;
(Continued)

(56) References Cited

U.S. PATENT DOCUMENTS

| 4,490,421 A | 12/1984 | Levy |
| RE32,983 E | 7/1989 | Levy |

(Continued)

FOREIGN PATENT DOCUMENTS

| CN | 101926698 A | 12/2010 |
| CN | 102596098 A | 7/2012 |

(Continued)

OTHER PUBLICATIONS

International Search Report and Written Opinion received for PCT Patent Application No. PCT/US2018/049983, dated Jan. 3, 2019, 13 pages.

(Continued)

*Primary Examiner* — Jerrah Edwards
*Assistant Examiner* — Jared Klar Rovira

(57) ABSTRACT

A medical device comprises a substrate (10) defining a major surface (9) defining a plane, including a plurality of first struts (14) along a first direction interconnected with a plurality of second struts (12) extending along a second direction not parallel with the first direction, wherein widths (11) of the second struts as measured along the major surface are larger than thicknesses of the second struts as measured perpendicular to the major surface such that when the substrate is stretched in the first direction, intermediate sections (15) of the second struts (12) rotate relative to the (Continued)

first struts (14) and the intermediate sections of the second struts bend out of the plane of the major surface. The medical device is operable to extend and/or retract elements suitable for a particular purpose. The elements are extended and/or retracted in response to a stress applied by way of stretching and/or retracting the device, among other methods. The elements may remain extended and/or retracted or may recoil back to an initial position upon the removal of the force. In various embodiments, the elements are used to treat or deliver treatment to a target site within a body.

16 Claims, 11 Drawing Sheets

(52) U.S. Cl.
CPC .. *A61F 2250/0067* (2013.01); *A61M 37/0015* (2013.01); *A61M 2037/0023* (2013.01)

(58) Field of Classification Search
CPC ...... A61F 2002/9155; A61F 2250/0031; A61F 2/92; A61F 2/915; A61F 2/848; A61F 2/91; A61F 2/2418; A61F 2230/0019; A61F 2/0063; A61F 2002/8483; A61M 2037/0023; A61M 2037/0046; A61B 17/320725; A61B 2017/22034
See application file for complete search history.

(56) References Cited

U.S. PATENT DOCUMENTS

| | | | |
|---|---|---|---|
| RE33,561 E | 3/1991 | Levy | |
| 5,320,634 A | 6/1994 | Vigil et al. | |
| 5,348,538 A | 9/1994 | Wang et al. | |
| 5,800,526 A | 9/1998 | Anderson et al. | |
| 6,066,167 A | 5/2000 | Lau et al. | |
| 6,197,013 B1 | 3/2001 | Reed et al. | |
| 6,419,692 B1* | 7/2002 | Yang | A61L 29/085 623/1.42 |
| 6,425,915 B1* | 7/2002 | Khosravi | A61F 2/92 623/1.22 |
| 6,991,617 B2 | 1/2006 | Hektner et al. | |
| 7,048,713 B2 | 5/2006 | Wang | |
| 7,063,639 B2 | 6/2006 | Schoenfelder et al. | |
| 7,303,572 B2 | 12/2007 | Melsheimer et al. | |
| 7,578,841 B2* | 8/2009 | Yadin | A61F 2/856 623/1.35 |
| 7,785,301 B2 | 8/2010 | Yuzhakov | |
| 8,636,696 B2 | 1/2014 | Ross et al. | |
| 8,764,712 B2 | 7/2014 | Melsheimer | |
| 8,864,780 B2* | 10/2014 | Euteneuer | A61F 2/0805 606/151 |
| 9,186,152 B2 | 11/2015 | Campbell et al. | |
| 9,308,007 B2 | 4/2016 | Cully et al. | |
| 9,333,101 B2 | 5/2016 | Shaw | |
| 9,381,326 B2 | 7/2016 | Cully et al. | |
| 9,585,647 B2* | 3/2017 | Clark | A61B 17/0057 |
| 9,737,422 B2* | 8/2017 | Armstrong | A61F 2/966 |
| 9,750,622 B2* | 9/2017 | Ma | A61L 31/041 |
| 2005/0080478 A1 | 4/2005 | Barongan | |
| 2005/0273049 A1 | 12/2005 | Krulevitch et al. | |
| 2006/0178685 A1 | 8/2006 | Melsheimer | |
| 2007/0191811 A1 | 8/2007 | Berglund | |
| 2010/0204779 A1 | 8/2010 | Schuessler et al. | |
| 2011/0004237 A1 | 1/2011 | Schneider et al. | |
| 2011/0166516 A1 | 7/2011 | Orr | |
| 2011/0264193 A1 | 10/2011 | Abunassar | |
| 2012/0035705 A1 | 2/2012 | Giasolli et al. | |
| 2012/0065649 A1 | 3/2012 | Towler | |
| 2012/0065660 A1 | 3/2012 | Ferrera et al. | |
| 2013/0116655 A1 | 5/2013 | Bacino et al. | |
| 2014/0046347 A1 | 2/2014 | Cully et al. | |
| 2014/0277562 A1 | 9/2014 | Seddon et al. | |
| 2015/0057743 A1 | 2/2015 | Ta et al. | |
| 2016/0015538 A1 | 1/2016 | Kariniemi et al. | |
| 2016/0346075 A1 | 12/2016 | Michalak | |
| 2017/0100266 A1 | 4/2017 | Fulkerson et al. | |
| 2017/0105724 A1 | 4/2017 | Limem et al. | |

FOREIGN PATENT DOCUMENTS

| | | |
|---|---|---|
| CN | 102740806 A | 10/2012 |
| CN | 103313681 A | 9/2013 |
| CN | 103547235 A | 1/2014 |
| CN | 105007842 A | 10/2015 |
| CN | 205054517 U | 3/2016 |
| CN | 106137481 A | 11/2016 |
| CN | 106714733 A | 5/2017 |
| CN | 106901881 A | 6/2017 |
| EP | 0732089 A2 | 9/1996 |
| EP | 1810642 A2 | 7/2007 |
| JP | 10-201856 A | 8/1998 |
| JP | 11-501526 A | 2/1999 |
| JP | 2002-253679 A | 9/2002 |
| JP | 2003-512887 A | 4/2003 |
| JP | 3519565 B2 | 4/2004 |
| JP | 2013-513441 A | 4/2013 |
| JP | 2016-511104 A | 4/2016 |
| JP | 2020-533116 A | 11/2020 |
| WO | 01/32099 A2 | 5/2001 |
| WO | 02/15821 A1 | 2/2002 |
| WO | 2007/111762 A1 | 10/2007 |
| WO | 2011/063412 A2 | 5/2011 |
| WO | 2014/100750 A1 | 6/2014 |
| WO | 2019/055311 A1 | 3/2019 |

OTHER PUBLICATIONS

International Preliminary Report on Patentability received for PCT Patent Application No. PCT/US2018/049983, dated Mar. 26, 2020, 9 pages.

K. Hassani, The effects of implanting different stents on the blood hemodynamic in coronary arteries, IEEE EMBS International Conference on Biomedical Engineering and Sciences, Langkawi, Dec. 31, 2012, pp. 479-483.

Wen Li, "Research progress of minimally invasive surgery and equipment," Foreign Medical Information, Dec. 31, 2005, pp. 11-13.

* cited by examiner

SUBSTRATE WITH ROTATABLE STRUTS FOR MEDICAL DEVICE

CROSS-REFERENCE TO RELATED APPLICATION

This application is a national phase application of PCT Application No. PCT/US2018/049983, internationally filed on Sep. 7, 2018, which claims the benefit of Provisional Application No. 62/557,488, filed Sep. 12, 2017, both of which are herein incorporated by reference in their entireties for all purposes.

FIELD

The present disclosure relates generally to medical devices.

SUMMARY

Various aspects of the present disclosure are directed toward a medical device including a substrate defining a major surface, the major surface defining a plane, the major surface including a plurality of first struts extending along a first direction that are interconnected with a plurality of second struts extending along a second direction not parallel with the first direction along the major surface. Widths of the second struts as measured along the major surface are larger than thicknesses of the second struts as measured perpendicular to the major surface such that when the substrate is stretched in the first direction, intermediate sections of the second struts rotate relative to the first struts and the intermediate sections of the second struts bend out of the plane of the major surface prior to the stretching.

In some embodiments, the medical device further comprises a plurality of projections extending from intermediate sections of the plurality of second struts. When the substrate is stretched along the second direction, the plurality of projections rotate with the intermediate sections of the plurality of second struts to project outwardly relative to the plurality of first struts.

The plurality of projections may optionally include anchors. In a variety of embodiments, such anchors may be operable to perform one or more of: anchor into tissue, deliver drugs to tissue, stimulate tissue, conceal tissue, expose tissue, secure tissues together, and secure tissue to a medical device, such as a graft or other component of an implantable medical device. In the same or different embodiments, such projections may represent the projections that includes microneedles operable to deliver a therapeutic fluid or collect a sample.

Various aspects of the present disclosure are also directed toward a medical system including a medical device of the preceding paragraphs, and a delivery device configured to induce the stretching of the substrate. A deployment of the medical device includes stretching of the substrate such that the second struts rotate relative to the first struts.

Various aspects of the present disclosure are also directed toward a medical system including a medical device of the preceding paragraphs, and a delivery device configured to deliver the medical device within a confined orifice of a patient. The substrate is a flat sheet curled up within the delivery device. The delivery device is operable to deploy the substrate within the confined orifice such that the flat sheet at least partially uncurls within the confined orifice. The medical device is configured to be used as a hernia patch with the plurality of projections being configured to contact or penetrate a tissue of the patient adjacent an opening in the tissue at a herniation.

Various aspects of the present disclosure are also directed toward a medical system including a medical device of the preceding paragraphs, and a delivery device configured to deliver the medical device within a vasculature of a patient with the medical device in a collapsed configuration. The delivery device is operable to deploy the tubular substrate within the vasculature. A deployment of the medical device includes stretching of the tubular substrate to an expanded configuration such that the second struts rotate relative to the first struts.

Various aspects of the present disclosure are also directed toward methods of manufacturing a medical device of the preceding paragraphs, the method comprising cutting a sheet of substrate material to form the substrate including the plurality of first struts and the plurality of second struts. The plurality of first struts are interconnected with the plurality of second struts in the cut sheet of substrate material.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
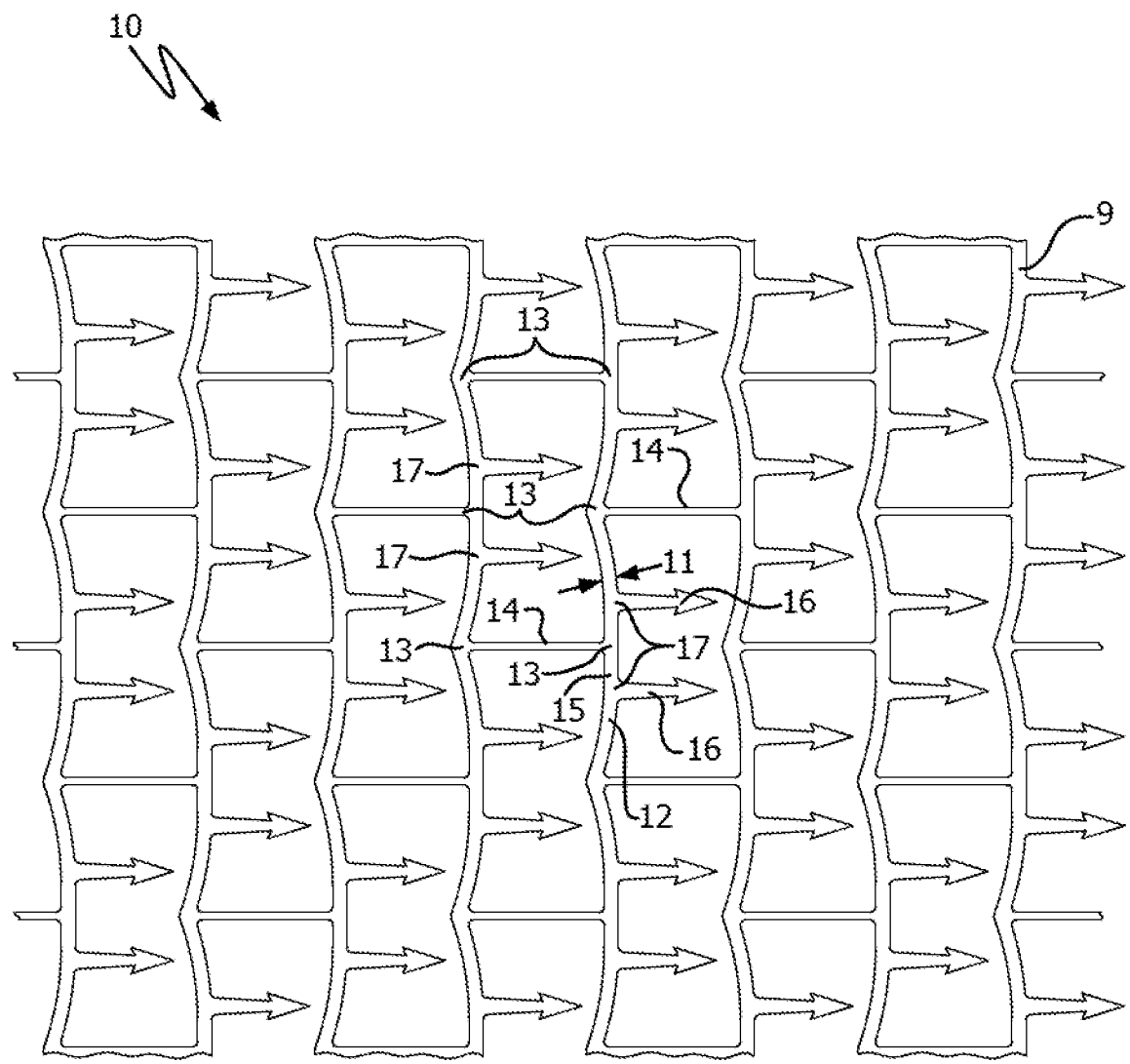
FIG. 1 illustrates an example substrate defining longitudinal and lateral struts in a major surface with barbed projections extending from intermediate sections of the lateral struts, in accordance with an embodiment.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Embodiments presented herein include a medical device operable to extend and/or retract elements suitable for a particular purpose. The elements are extended and/or retracted in response to a stress applied by way of stretching and/or retracting the device, among other methods. The elements may remain extended and/or retracted or may recoil back to an initial position upon the removal of the force. In various embodiments, the elements are used to treat or deliver treatment to a target site within a body. In the same or different embodiments, the elements may provide fixation for the medical device.

FIG. 1 illustrates an example substrate 10 defining a major surface 9 including a plurality of lateral struts 12 and a plurality of longitudinal struts 14. Lateral struts 12 extend along a first direction and are interconnected with longitudinal struts 14, which extend along a second direction not parallel with the first direction along the major surface 9. In some but not all embodiments, the first direction may be about perpendicular to the second direction. The substrate 10 is configured such that when the substrate 10 is stretched along a longitudinal direction, a direction perpendicular to the first direction, the lateral struts 12 rotate relative to the longitudinal struts 14 and bend out of a plane defined by the major surface 9 prior to the stretching. As referred to herein stretching along a direction means at least a part of the stretching is within the dimension of the direction, that is, the stretching, as a whole, need not be perpendicular to the direction.

The rotation of the lateral struts 12 occurs in response to stretching along the longitudinal direction as a result of the widths 11 of lateral struts 12 as measured along the major surface 9 being larger than thicknesses (not shown in FIG. 1) of lateral struts 12 measured perpendicular to the major surface 9. The widths only need to be marginally larger than the thicknesses as rotation occurs once the bending resistance across the thickness is less than bending resistance across the width of a strut; however, the designed width and thickness should account for any manufacturing tolerances to have reliable rotation for all of the lateral struts in response to the stretching of the substrate 10. At least the intermediate sections 15 of the lateral struts 12 are configured to rotate relative to the longitudinal struts 14 and bend out of the plane of the major surface 9, the plane being defined prior to the stretching, when substrate 10 is exposed to a stretching force. In conjunction with or following the rotation of the intermediate sections 15 of the lateral struts 12, the intermediate sections 15 of the lateral struts 12 bend in a plane parallel to the widths of the lateral struts 12 in conjunction with elongation of the substrate 10, for example, as shown in FIGS. 2C and 2D. The plane parallel to the widths of the lateral struts 12 includes major surface 9 at the lateral struts 12 and is generally parallel to the plane defined by directions 30, 32 for a planar substrate 10.

In some examples, all or substantially all of the lateral struts 12 are configured to rotate relative to the longitudinal struts 14 and bend out of the plane of the major surface 9 when exposed to a stretching force. In such examples, such as the example substrate 40 of FIGS. 3A-3B, longitudinal struts 14 or the strut interconnections 13 between longitudinal struts 14 and lateral struts 12 bend to allow the rotation of substantially all potions of lateral struts 12. In other examples, lateral struts 12 may twist to facilitate rotation of the intermediate sections 15 of the lateral struts. In such examples, the strut interconnections 13 may be reinforced to resist bending of longitudinal struts 14 or the strut interconnections 13 between longitudinal struts 14 and lateral struts 12. Such reinforcement may include a widening of longitudinal struts 14 (e.g., in the plane of directions 30, 32) relative to lateral struts 12 as compared to the examples of FIGS. 1-3B.

In the example of FIG. 1, barbed projections 16 extend from intermediate sections 15 of the lateral struts 12. When the substrate 10 is stretched along a longitudinal direction, the barbed projections 16 rotate with the lateral struts 12 relative to the longitudinal struts 14 to project outwardly relative to the longitudinal struts 14, as shown in FIGS. 2A-2D. The magnitude of rotation is controllable by the magnitude of stretching along the longitudinal direction.

In addition, the rotation of the projections 16 may be augmented by providing the lateral struts 12 with a predetermined geometry, as with the example of the substrate 10. Specifically, each of the lateral struts 12 define a geometry that alternately extends at an angle to a transverse direction defining a serpentine portion with peaks and valleys with longitudinal struts 14 interconnecting lateral struts 12 adjacent apexes of the peaks and valleys. Projection interconnections 17 between lateral struts 12 and projections 16 are between the apexes of the peaks and valleys. Such a configuration can increase the degree of rotation of the projections 16 when the substrate 10 is stretched along a longitudinal direction as compared to embodiments in which the lateral struts 12 do not incorporate peaks and valleys. In the specific embodiment of FIG. 1, the serpentine portion of lateral struts 12 includes V-shaped portions including the peaks and valleys. In other embodiments, the serpentine portion of lateral struts 12 may include U-shaped portions including the peaks and valleys, or other configurations.

In the embodiment of FIG. 1, barbed projections 16 extend along the major surface 9 in a direction that is about parallel to longitudinal struts 14. The substrate 10, including the major surface 9, may be about flat. As such, the substrate 10 defining the lateral struts 12, longitudinal struts 14, and optionally all or a portion of barbed projections 16 may be cut from a flat sheet. In an alternative embodiment, the substrate 10, including the major surface 9, may be tubular such that lateral struts 12, longitudinal struts 14, and optionally all or a portion of barbed projections 16 may be cut from a tube. In either embodiment, relatively simple manufacturing techniques may be utilized to make the medical device that is operable to provide rotatable lateral struts 12 with projections 16, which are configured to rotate relative to the longitudinal struts 14 and relative to the original major surface 9 in response to longitudinal stretching of the substrate material.

Figure 7A:
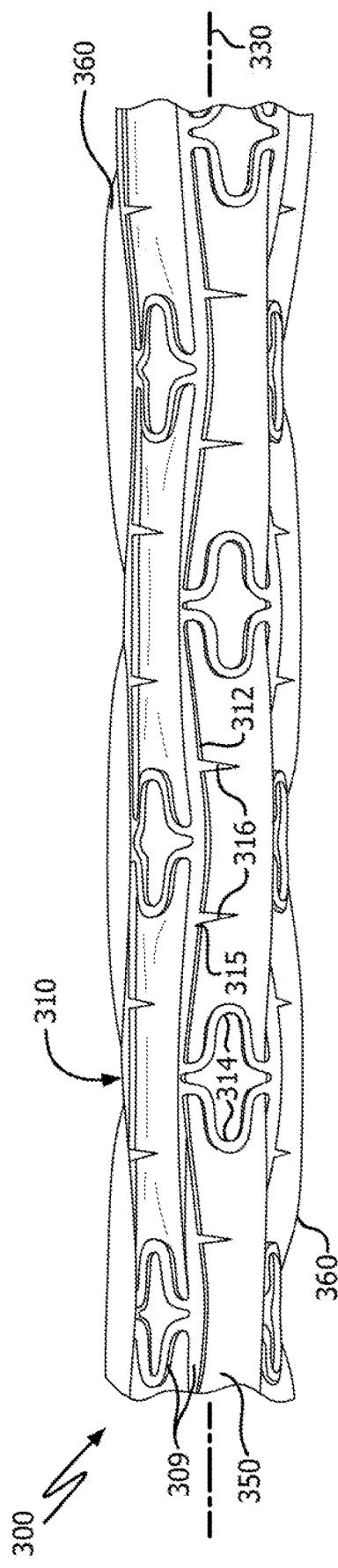
FIGS. 7A and 7B illustrate a balloon inflatable vascular drug delivery system including a substrate defining circumferential and lateral struts in a tubular major surface with projections extending from rotatable intermediate sections of the lateral struts, in accordance with an embodiment.
Figure 7B:
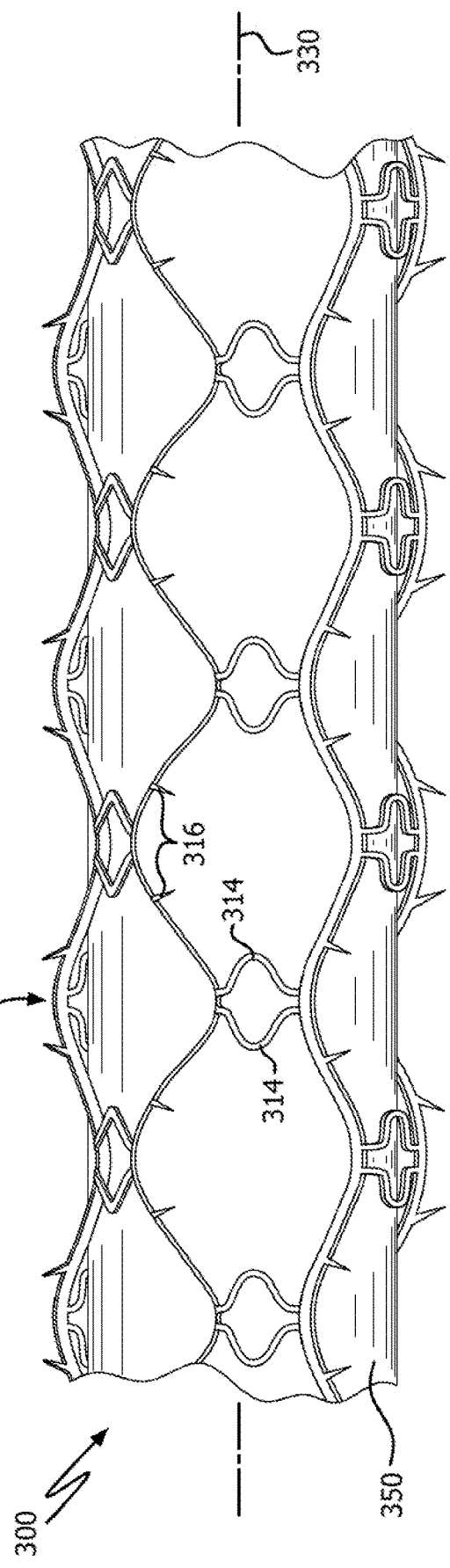

With respect to embodiments including a substrate 10 cut from a tube, referred herein as a tubular substrate 10a, the pattern of cuts to form lateral struts 12, longitudinal struts 14 optionally all or a portion of barbed projections 16 may be oriented in any direction about the major surface, such that radial stretching, for example, as shown FIGS. 7A and 7B, stretching along a length of the tubular substrate 10a, or a combination thereof may result in the rotation of barbed projections 16.

The tubular substrate 10a defining lateral struts 12 and longitudinal struts 14 defines a tubular major surface defining a longitudinal axis. In such embodiments, projections 16 may extend about parallel to the longitudinal axis when the tubular substrate 10a is in the unstretched condition, and the projections 16 may extend radially outward when the tubular substrate 10a is stretched in the longitudinal direction parallel with the longitudinal axis. Some or all of projections 16 may also be oriented to extend inward when the tubular substrate 10a is stretched in the longitudinal direction.

Example steps for manufacturing a medical device including the substrate 10 may include cutting a sheet of substrate material to form the substrate 10 including the longitudinal struts 14 and lateral struts 12 with strut interconnections 13, as well as barbed projections 16 or base portions of barbed projections 16, i.e., the portions connected to intermediate sections 15. As discussed above, longitudinal struts 14 may be interconnected with lateral struts 12 in the cut sheet of substrate material according to the pattern of the cutting to provide strut interconnections 13. In addition, also according to the pattern of the cutting, barbed projections 16 extend from the intermediate sections 15 of lateral struts 12 in the cut sheet of substrate material. In various embodiments, the sheet of substrate material may be a tubular sheet of substrate material or a flat sheet of substrate material. In a tubular sheet of substrate material, lateral struts 12 and/or longitudinal struts 14 may form tubular or generally helical rings according to the pattern of the cutting.

The method may further include stretching the substrate 10 along a direction perpendicular to the longitudinal direction, i.e., in a direction nonparallel to the longitudinal direction, to rotate the lateral struts 12 relative to the longitudinal struts 14 and rotate the projections 16 relative to the longitudinal struts 14. In conjunction with or following the rotation of the intermediate sections 15 of the lateral struts 12, the intermediate sections 15 of the lateral struts 12 bend in a plane parallel to the widths of the lateral struts 12 in conjunction with elongation of the substrate 10, for example, as shown in FIGS. 2C and 2D. Such stretching may be reversible in that it results in elastic deformation of the substrate 10, or nonreversible in that it results in plastic deformation of the substrate 10.

The material of the substrate 10 may include one or more of metal, such as stainless steel, plastic, superelastic metal, such as nitinol, and/or shape memory materials, such as nitinol. In embodiments in which the substrate 10 includes nitinol, or another elastic material, substrate 10 may be configured to self-expand to elongate the substrate 10 and rotate the lateral struts 12 relative to the major surface 9 of the longitudinal struts 14, for example, such that projections 16 are biased to protrude relative to the longitudinal struts 14. As another example, an elastic substrate 10 may be configured to self-contract to retract the substrate 10, for example, such that projections 16 are biased to lay flat relative to the major surface 9 of the longitudinal struts 14. Such stretching may be at least predominantly due to mechanical energy rather than thermal energy, although in some examples the nitinol substrate may be temperature-activated.

Barbed projections 16 represent anchors including pointed tips with barbs suitable to impede retraction of projections 16 once deployed within a tissue. Barbed projections 16 and other such anchors are operable to penetrate at least one of tissue of a patient and graft material of an implantable medical device, such a graft material of a heart valve device as part of a valve-in-a-valve implantation procedure. In some embodiments, projections 16 may be deployable by stretching of the substrate 10, and retractable by either compressing the substrate 10, or by removing a stretching force from the substrate 10.

In different configurations, the projections 16 configured as anchors are operable to perform one of more of: anchor into tissue, deliver drugs to tissue (for example, as discussed in further detail with respect to FIGS. 7A and 7B), stimulate tissue when coupled to a stimulation generator of a medical device, conceal tissue, expose tissue, secure tissues together, and secure tissue to a medical device, such as a graft or other component of an implantable medical device.

Figure 2A:
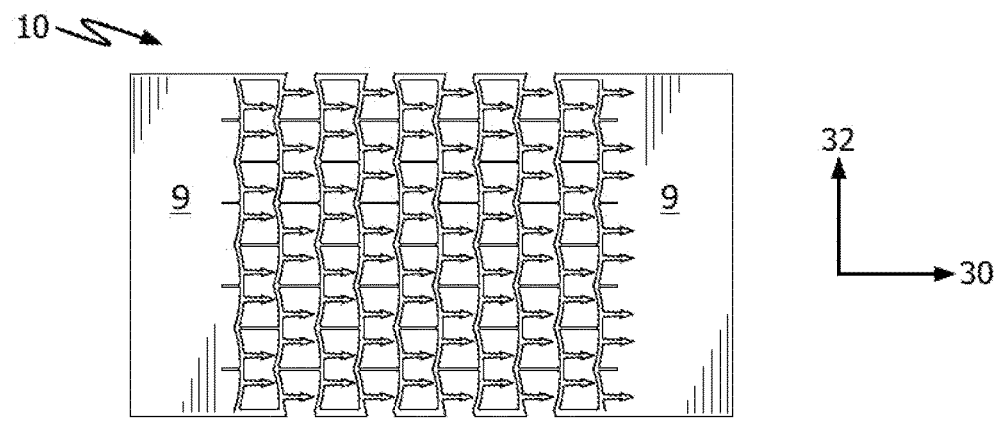
FIGS. 2A-2D illustrate rotation of the barbed projections of the example substrate of FIG. 1 after stretching the substrate along a longitudinal direction from an initial state.
Figure 2B:
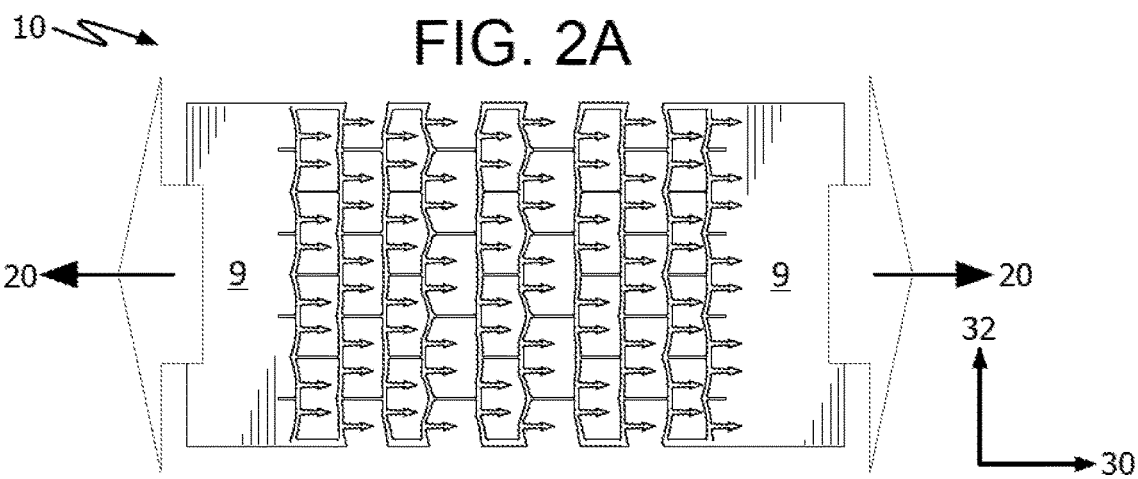
Figure 2C:
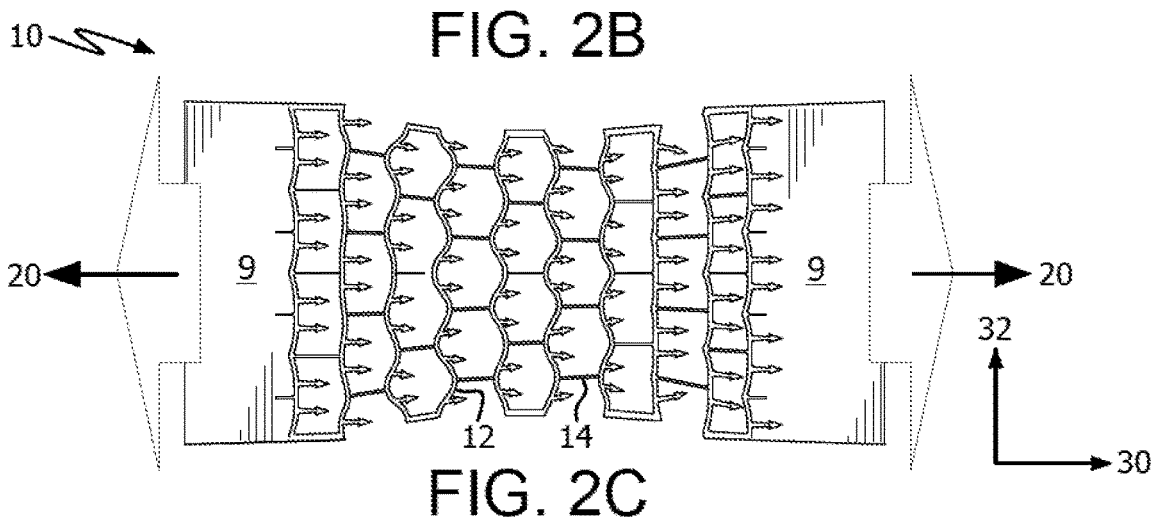
Figure 2D:
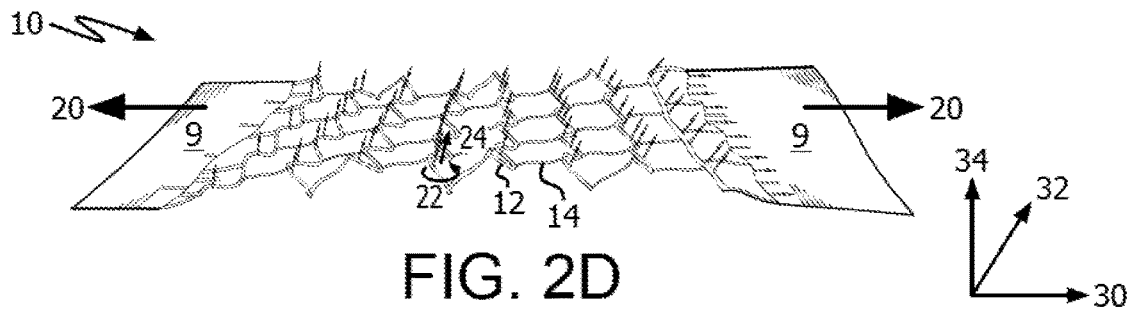

FIGS. 2A-2D illustrate rotation of the barbed projections 16 of the substrate 10 by stretching the substrate 10 along a longitudinal direction 30, such as in a non-perpendicular direction relative to longitudinal direction 30. FIG. 2A is a top view illustration of the substrate 10 in a flat pattern including longitudinal struts 14, lateral struts 12 and barbed projections 16 as cut in a flat sheet of substrate material. Longitudinal direction 30 and lateral (width) direction 32 are indicated and represent the major surface 9 including the longitudinal struts 14, the lateral struts 12, and the projections 16.

FIG. 2B is a top view illustration of the application of a force 20 along longitudinal direction 30 to stretch the substrate 10 along longitudinal direction 30. FIG. 2C illustrates additional application of force 20 to stretch the substrate 10 further along longitudinal direction 30. FIG. 2D is a side view illustration of the substrate 10 stretched along longitudinal direction 30 as shown in FIG. 2C. As shown in FIG. 2D, rotation 22 of the lateral struts 12 and the projections 16 has occurred relative to the longitudinal struts 14 from the stretching of the substrate 10 along the longitudinal direction 30 such that projections 16 point in direction 24, which is outwardly relative to the unstretched plane of the substrate 10, including the lateral struts 12, and the projections 16. Such rotation occurs because widths 11 of lateral struts 12 as measured along the major surface 9 are larger than thicknesses of lateral struts 12 measured perpendicular to the major surface 9 along direction 34 such that lateral struts 12 are biased to bend within the thickness direction 34 rather than the width direction 32. The intermediate sections 15 of the lateral struts 12 bend in a plane parallel to the widths of the lateral struts 12 in conjunction with elongation of the substrate 10 along longitudinal direction 30.

The rotation is augmented by the geometry of lateral struts 12, in that each of lateral struts 12 is nonlinear along the major surface 9 such that intermediate sections 15 of lateral struts 12 are offset from the strut interconnections 13 between lateral struts 12 and longitudinal struts 14 to accentuate the rotation of the projections 16 from the stretching of the substrate 10 along longitudinal direction 30.

When the substrate 10 is stretched along longitudinal direction 30, intermediate sections 15 of lateral struts 12 rotate relative to longitudinal struts 14 and bend out of the plane of the major surface 9. In some example, only a portion of lateral struts 12 rotate relative to longitudinal struts 14 with other portions of lateral struts 12 twisting to allow the rotation. In other examples, longitudinal struts 14 may bend to allow most or all portions of lateral struts 12 to rotate relative to longitudinal struts 14. In conjunction with or following the rotation of the intermediate sections 15 of the lateral struts 12, the intermediate sections 15 of the lateral struts 12 bend in a plane parallel to the widths of the lateral struts 12 in conjunction with elongation of the substrate 10 along longitudinal direction 30, for example, as shown in FIGS. 2C and 2D. The magnitude of rotation is controllable by the magnitude of stretching along the longitudinal direction.

The substrate 10 as shown represent an example of various features of a substrate and, although the combination of those illustrated features is clearly within the scope of invention, that example and its illustration is not meant to suggest the inventive concepts provided herein are limited from fewer features, additional features, or alternative features to one or more of those features shown in FIGS. 1 and 2A-2D. For example, in various embodiments, the major surface of the substrate 10 may instead be a tubular major surface rather than the planar major surface 9.

EMBODIMENTS

Embodiment 1

Figure 3A:
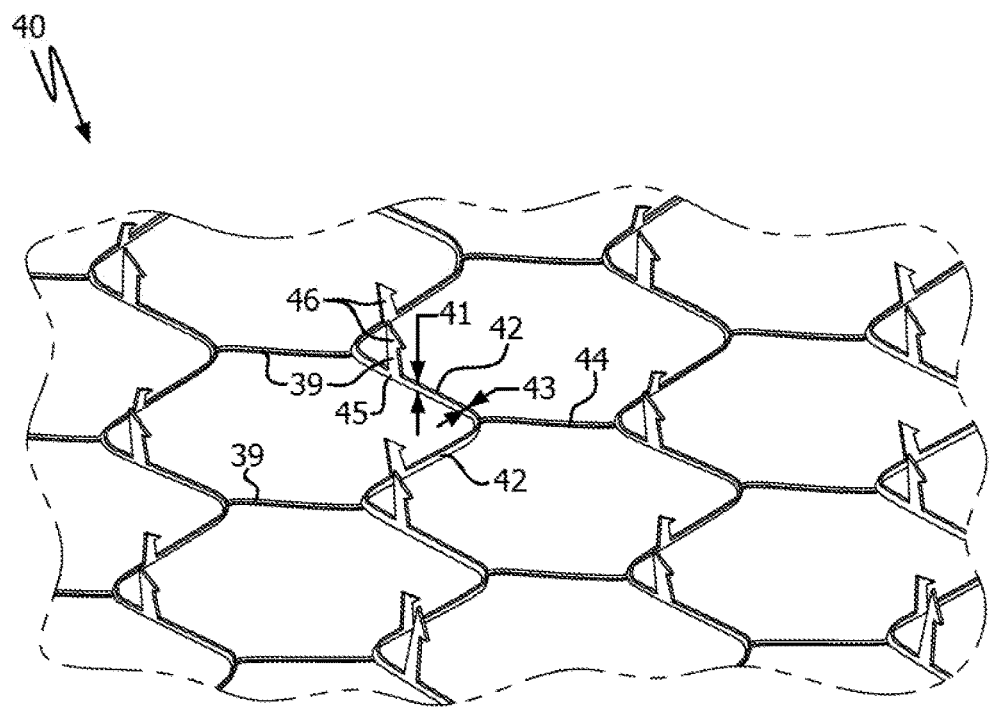
FIGS. 3A and 3B illustrate an example substrate defining longitudinal and lateral struts in a major surface with barbed projections extending from intermediate sections of the lateral struts, in accordance with an embodiment.
Figure 3B:
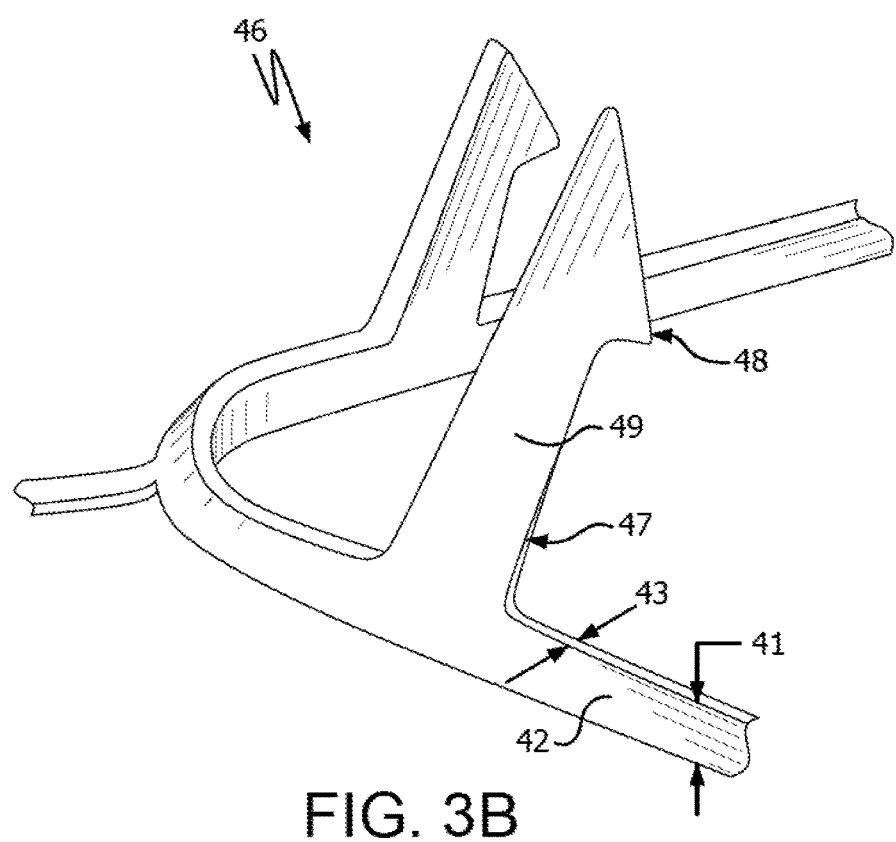

FIGS. 3A and 3B illustrate an example stainless steel substrate 40 defining longitudinal struts 44 and lateral struts 42 in a major surface 39 with barbed projections 46 extending from intermediate sections 45 of the lateral struts 42. In some embodiments, substrate 40 may be a stainless steel substrate. Substrate 40 is shown as stretched along a longitudinal direction. In an unstretched configuration (not shown), the widths 41 of lateral struts 42 as measured along the major surface 39 are larger than the thicknesses 43 of lateral struts 42 as measured perpendicular to the major surface 39.

In the embodiment of FIGS. 3A and 3B, substantially all portions of the lateral struts 42, including the intermediate sections 45 of the lateral struts 42, are configured to rotate relative to the longitudinal struts 44 and bend out of the plane of the major surface 39 when substrate 40 is exposed to a stretching force. In conjunction with or following the rotation of the intermediate sections 45 of the lateral struts 42, the intermediate sections 45 of the lateral struts 42 bend in a plane parallel to the widths of the lateral struts 42 in conjunction with elongation of the substrate 40. The plane parallel to the widths of the lateral struts 42 includes major surface 39 at the lateral struts 42.

Substrate 40 is substantially similar to the substrate 10 except that it is configured to facilitate near perpendicular orientation of projections 46 relative to the major surface 39 of longitudinal struts 44 when stretched. Barbed projections 46 and other such anchors are operable to penetrate tissue of a patient. As with barbed projections 16, barbed projections 46 represent anchors suitable to impede retraction, and potentially prevent pullout of projections 46 once deployed within a patient tissue. In some embodiments, projections 16, 46 may be deployable by stretching of substrate 40, and retractable by either compressing substrate 40, or by removing a stretching force from substrate 40. The magnitude of rotation is controllable by the magnitude of stretching along the longitudinal direction.

As shown in FIG. 3B, projections 46 each include a base portion 47, a tip end portion 48 distal to the base portion, and a body portion 49 between the base portion and the tip end portion. At least the base portion 47 is integral with the transverse strut 42. Although, one or both of tip end portion 48 and body portion 49 may also be integral with the transverse strut 42.

Figure 8A:
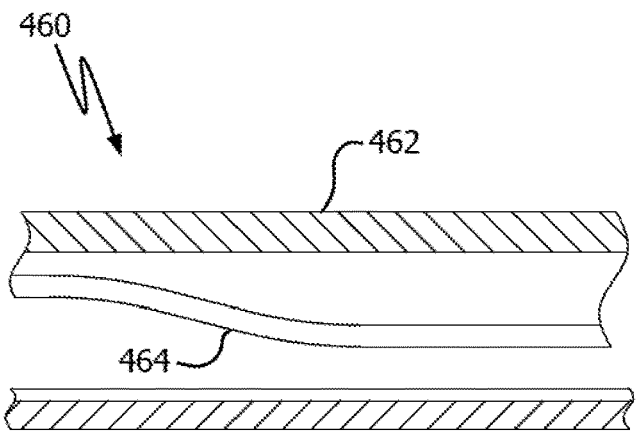
FIGS. 8A-8D illustrate deployment of barbed sleeves from projections operable to secure two tissue layers together, in accordance with an embodiment.
Figure 8D:
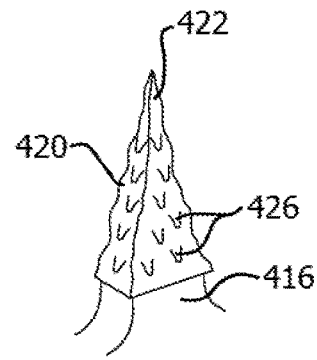
Figure 8B:
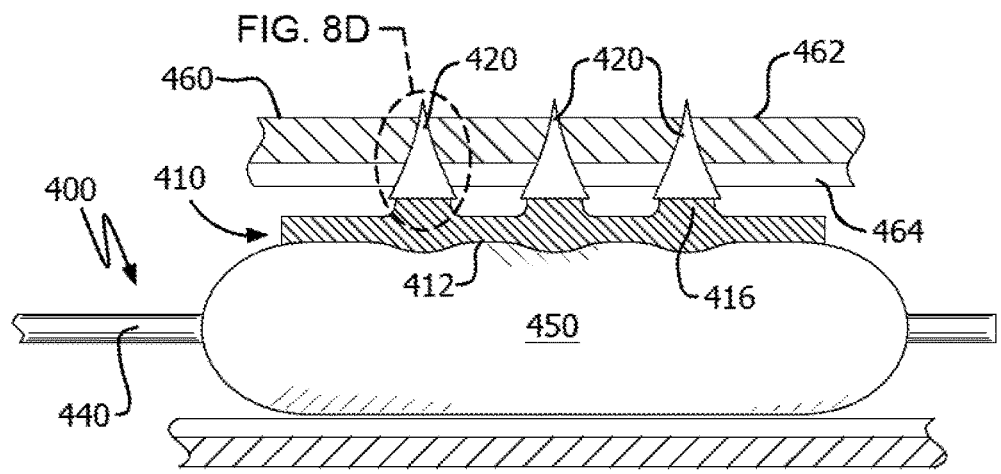
Figure 8C:
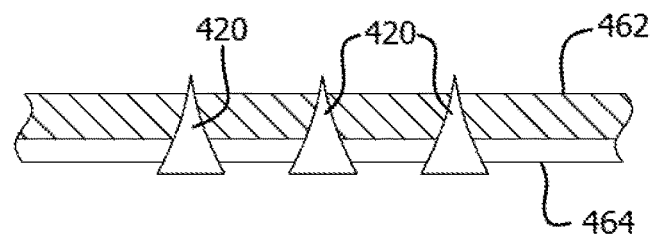
Figure 8C:
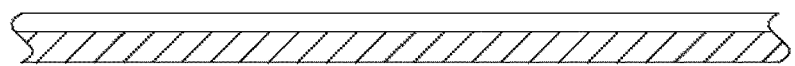
Figure 9A:
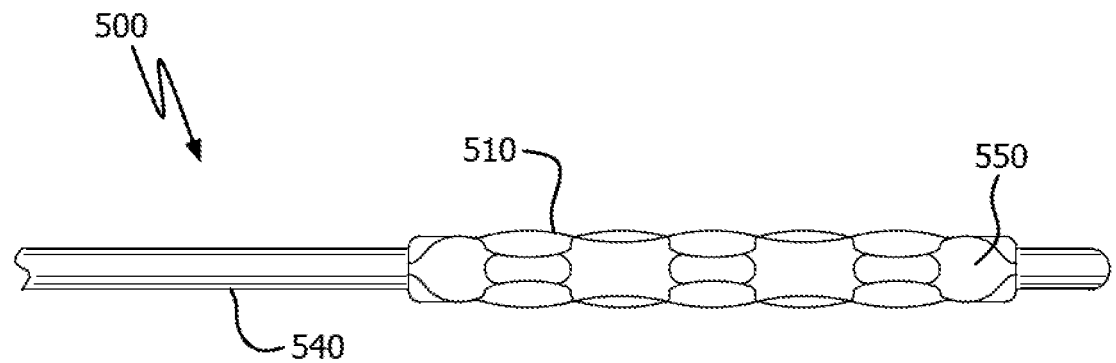
FIGS. 9A-9D illustrate a medical device suitable for endoluminal delivery, the medical device including a diametrically adjustable tubular substrate with rotatable struts mounted on an elongated member, in accordance with an embodiment.
Figure 9B:
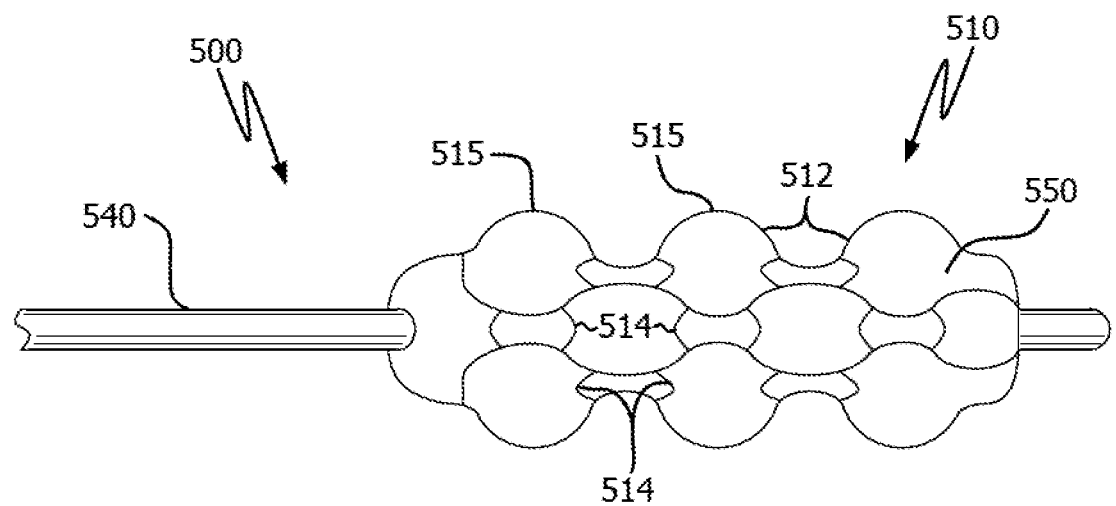
Figure 9C:
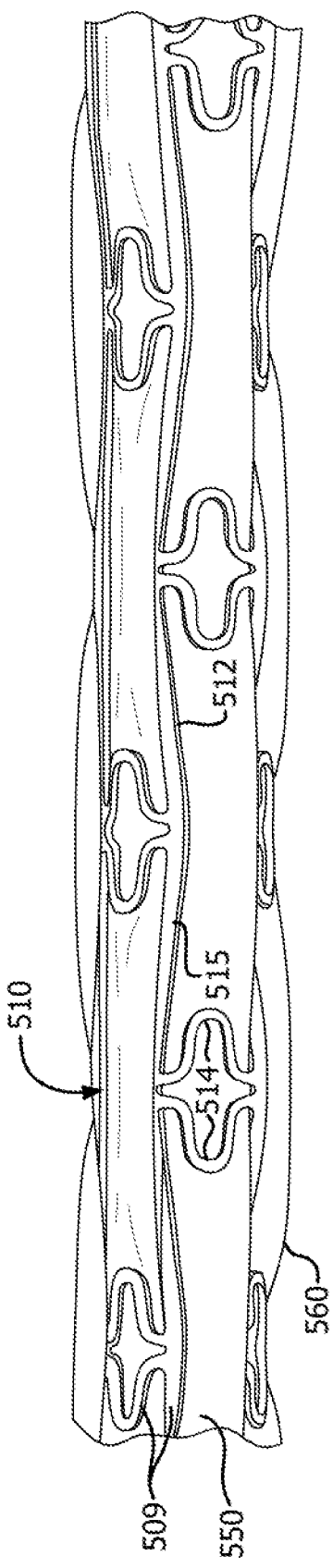
Figure 9D:
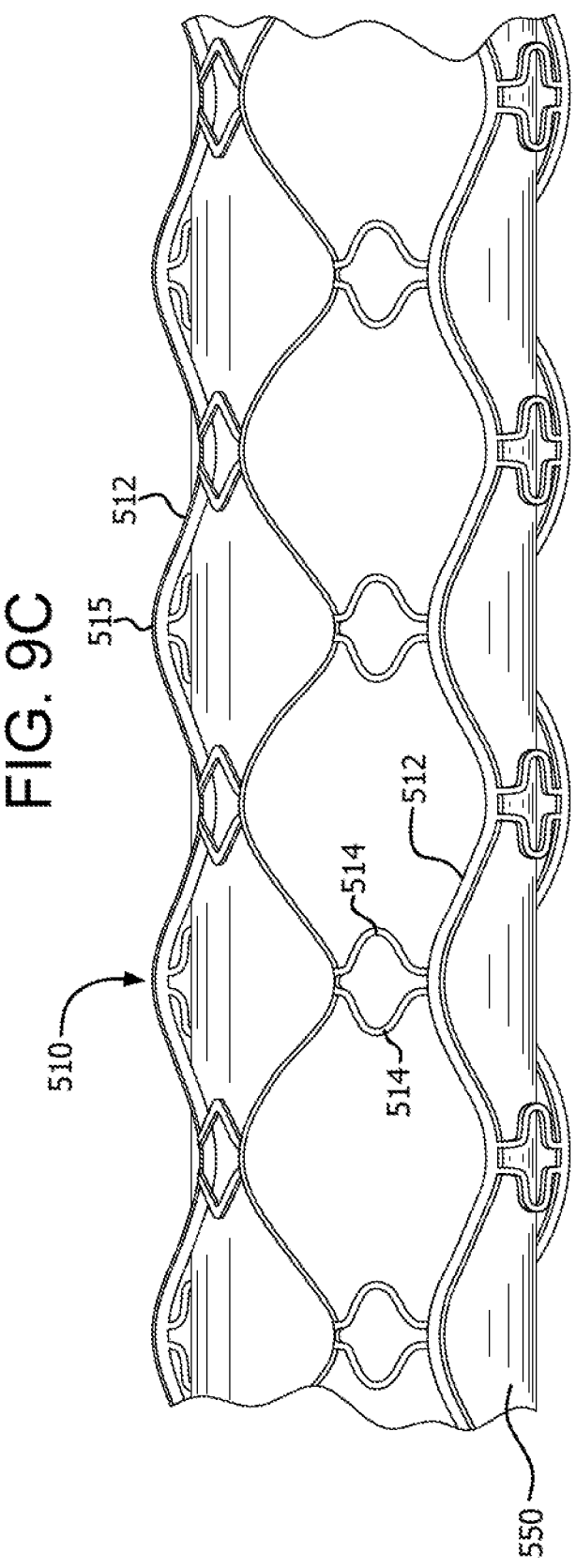

Substrates 10, 40 are suitable for use in a medical device in a variety of configurations for any number of applications. In some embodiments, projections 46 may include a removable distal section, such as a coating, a cap or a distal tip. In different embodiments, the removable distal section may include one or more of: an erodible portion, an absorbable portion, a break-off distal portion, a tacky distal portion, a barbed, break-off distal tip, a cap or a barbed sleeve (as shown in FIGS. 8A-8C), biological moieties, or other removable distal section. In any of these embodiments, the removable distal section may include a therapeutic compound.

In various embodiments, the form of a tip end portion 48 may be pointed, configured as an arrowhead, a single-sided arrowhead, barbed, textured, rectangular, square, oval, circular, diamond, triangular, elliptical, polygonal, U-shaped, star-shaped, or in any other configuration suitable for the selected application. A variety of different projection configurations suitable for use with tubular or flat substrates 10, 40 are illustrated in FIGS. 4A-4K.

Figure 4A:
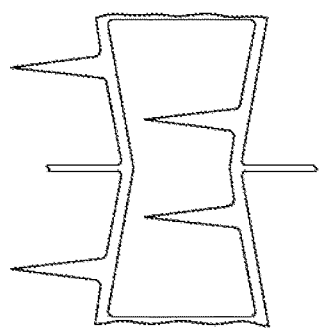
FIGS. 4A-4K illustrate example projection configurations suitable for use with a substrate providing rotatable struts with projections, in accordance with various embodiments.

The projections of FIG. 4A provide triangular profiles.

Figure 4B:
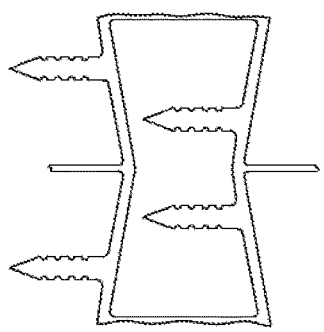

The projections of FIG. 4B provide pointed tips with serrated edges.

Figure 4C:
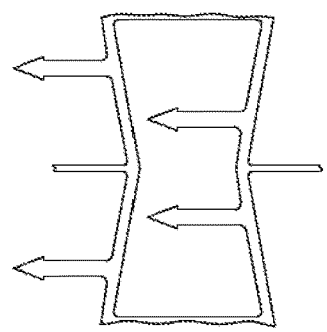

The projections of FIG. 4C provide symmetric barbed tips, i.e., arrowhead.

Figure 4D:
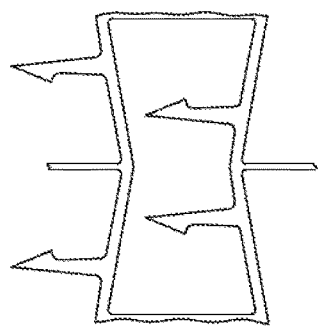

The projections of FIG. 4D provide asymmetric barbed tips, i.e., single sided arrowhead.

Figure 4E:
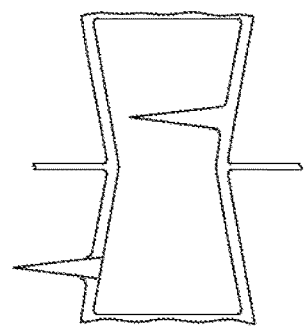

The projections of FIG. 4E provide triangular profiles in an asymmetric arrangement relative to the longitudinal struts.

Figure 4F:
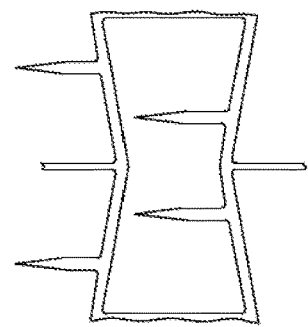

The projections of FIG. 4F provide pointed tips.

Figure 4G:
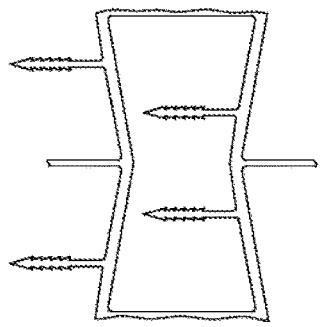

The projections of FIG. 4G provide pointed tips with a series of barbs between the pointed tips and the lateral struts.

Figure 4H:
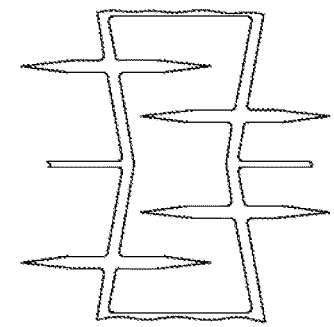

The projections of FIG. 4H include coincident projections that extend on both sides of the lateral struts such that the projections are configured to rotate relative to the longitudinal struts and point out of opposing sides relative to the longitudinal struts when the substrate is stretched.

Figure 4I:
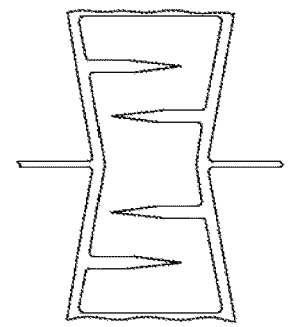

The projections of FIG. 4I include projections that extend on opposing sides of alternating lateral struts such that the projections are configured to rotate relative to the longitudinal struts and point out of opposing sides relative to the longitudinal struts when the substrate is stretched.

Figure 4J:
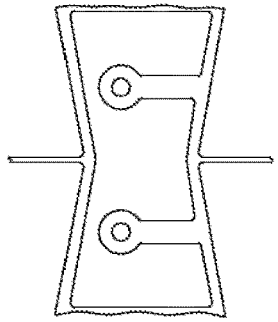

The projections of FIG. 4J include apertures which facilitate connecting or threading something through the projections.

Figure 4K:
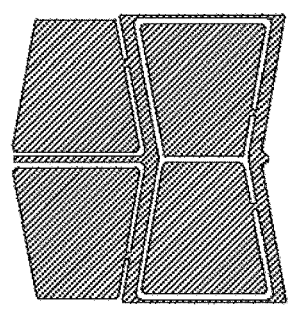

The projections of FIG. 4K include rotating paddles which facilitate revealing and obscuring something by the rotation of the paddles.

Embodiment 2

Figure 5A:
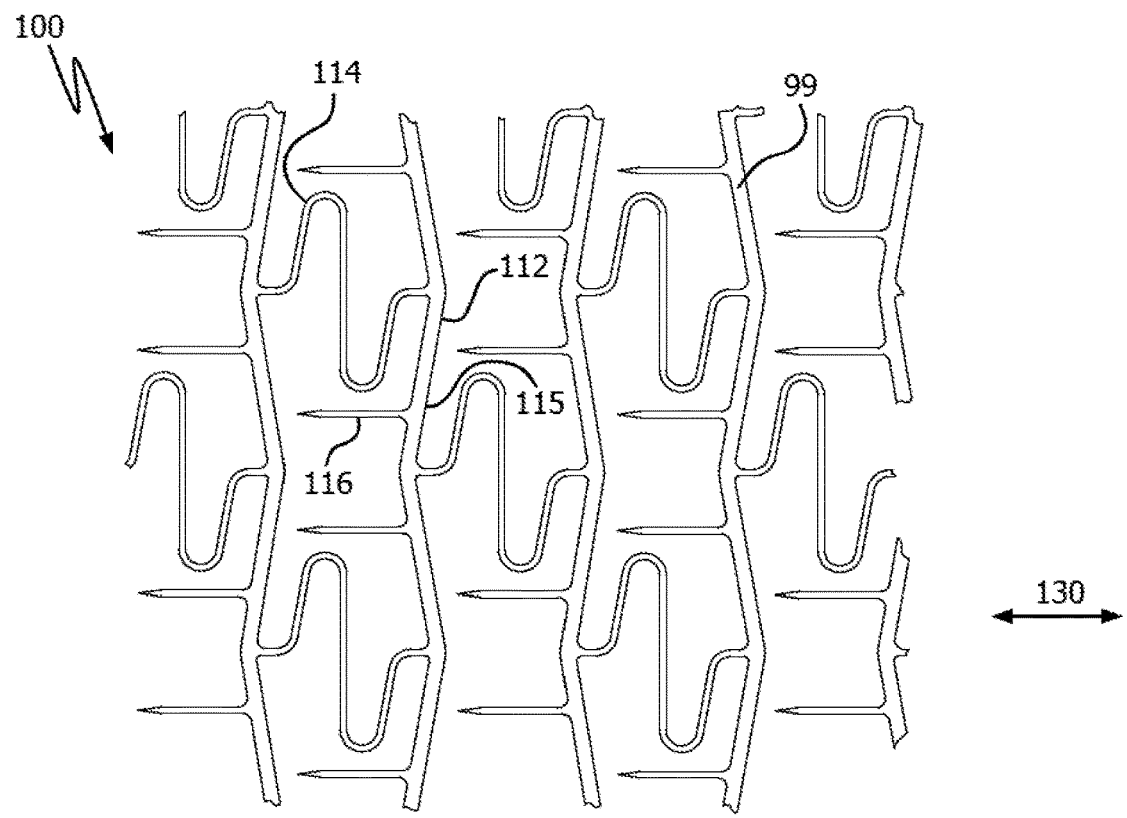
FIGS. 5A and 5B illustrate an example substrate defining serpentine longitudinal struts and lateral struts in a major surface with projections extending from rotatable intermediate sections of the lateral struts, in accordance with an embodiment.
Figure 5B:
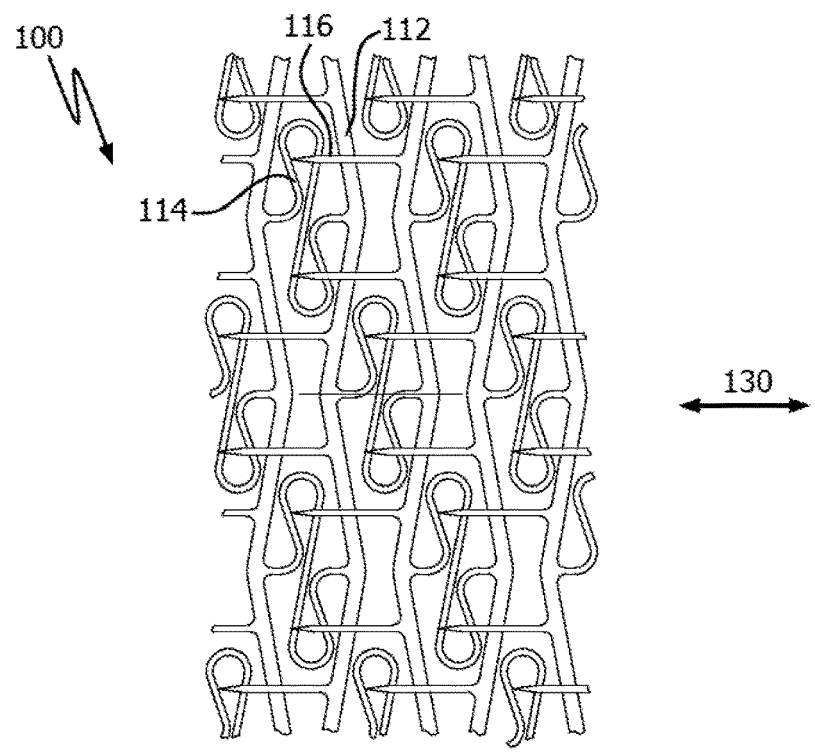

FIGS. 5A and 5B illustrate an example substrate 100 defining a major surface 99 including serpentine longitudinal struts 114 and lateral struts 112 with projections 116 extending from rotatable intermediate sections 115 of the lateral struts 112. With the exception of serpentine longitudinal struts 114, the substrate 100 is otherwise similar to substrates 10, 40 and the serpentine longitudinal struts 114 may be combined with elements and features previously described with respect to substrates 10, 40 by replacing with longitudinal struts 14 or longitudinal struts 44 with serpentine longitudinal struts 114. FIG. 5A illustrates serpentine longitudinal struts 114 in an extended configuration, whereas FIG. 5B illustrates serpentine longitudinal struts 114 in a collapsed configuration.

The longitudinal struts 114 have a curved shape operable to allow compression and expansion of the longitudinal struts 114 along the longitudinal direction 130 prior to rotation of the lateral struts 112. For example, initial stretching of substrate 100 along direction 130 may straighten the longitudinal struts 114 without rotation of the lateral struts 112. But following the straightening or partial straightening of the longitudinal struts 114, further stretching of substrate 100 along direction 130 may result in rotation of lateral struts 112 and projections 116 as previously described herein.

Substrate 100 is similar to substrates 10, 40 and substrates 10, 40 may be combined with elements and features with respect to substrate 100 by including serpentine longitudinal struts with any of the features or elements described with respect to substrates 10, 40.

Embodiment 3

Figure 6:
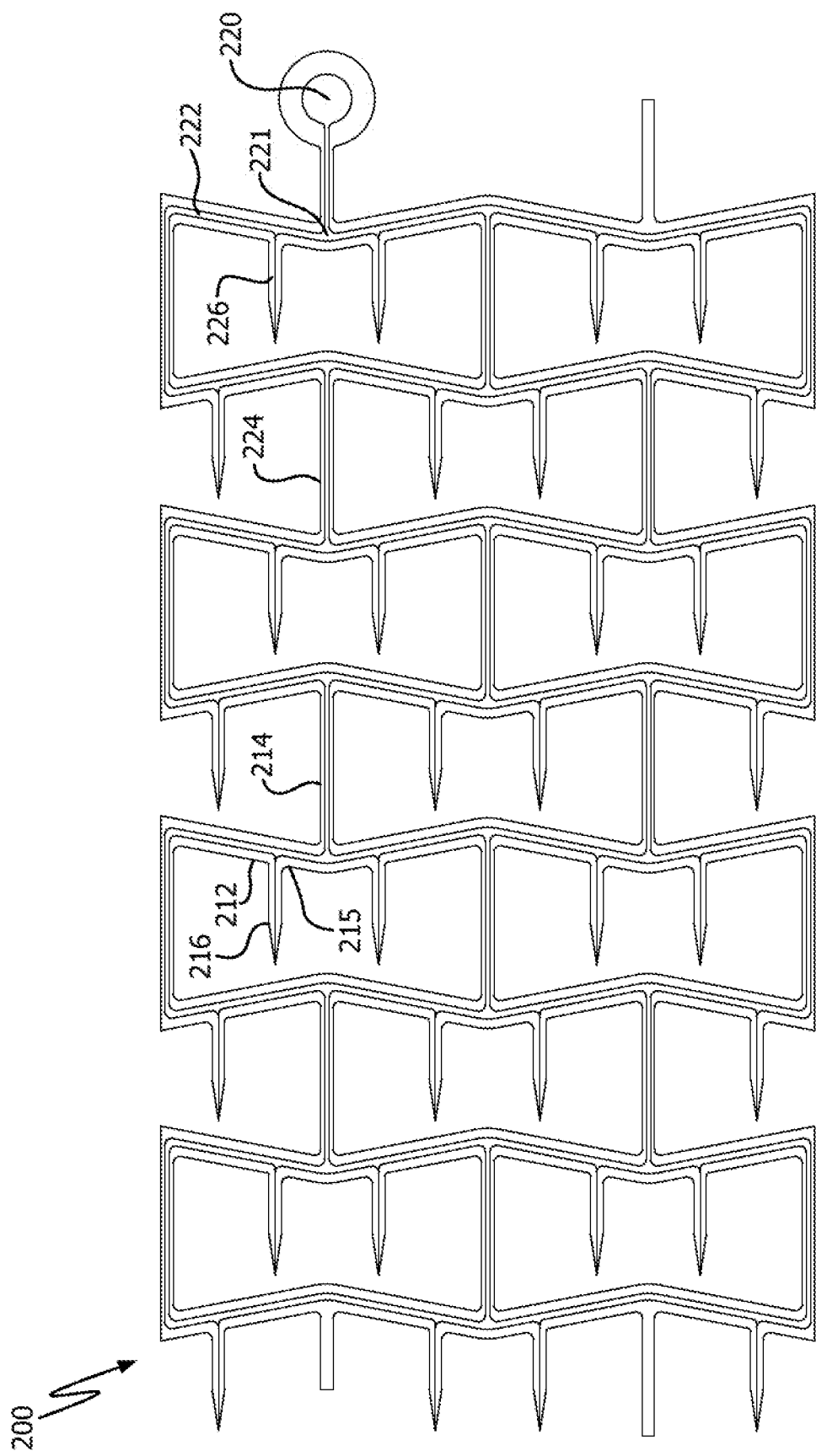
FIG. 6 illustrates an example substrate defining longitudinal and lateral struts in a major surface with microneedle projections extending from rotatable intermediate sections of the lateral struts, the struts including lumens in fluid communication with the microneedle projections, in accordance with an embodiment.

FIG. 6 illustrates an example substrate 200 defining longitudinal struts 214 and rotatable lateral struts 212 with microneedle projections 216 extending from intermediate sections 215 of the lateral struts 212. Microneedle projections 216 are operable to deliver a therapeutic fluid or collect a fluid sample, with at least some of the lateral struts 212 and longitudinal struts 214 being of tubular construction and in fluid communication with microneedle projections 216.

As shown, longitudinal struts 214 include lumens 224, and lateral struts 212 include lumens 222. Lumens 222, 224 are in fluid communication with central lumens 226 of microneedle projections 216 and with fluid repository 220 via manifold 221. In various embodiments, fluid repository 220 may be used to deliver and or collect fluid via central lumens 226 of microneedle projections 216. With the exception of lumens 222, 224 and central lumens 226, substrate 200 is otherwise similar to substrates 10, 40, and the microneedle projections 216 may be combined with elements and features previously described with respect to substrates 10, 40.

In some embodiments, the fluid repository 220 is located adjacent a proximal end of a medical device including the substrate 200. In other embodiments, the fluid repository 220 is located adjacent a proximal end of a delivery device suitable to facilitate delivery of a medical device including the substrate 200. Such a delivery device may be configured to induce the stretching of the substrate 200. For example, the delivery device may include an elongated element to stretch the medical device in a longitudinal direction parallel to a major axis of the delivery device. In the same or different embodiments, delivery device may include a balloon to radially or longitudinally stretch the substrate 200 in conjunction with or following the release of the medical device from a distal end of a tubular delivery element of the delivery device. In such balloon deployment embodiments, substrate 200 may be a tubular substrate.

Substrate 200 is similar to substrates 10, 40, 100 and substrates 10, 40, 100 may be combined with elements and features with respect to substrate 200 by including microneedle projections and lumens with any of the features or elements described with respect to substrates 10, 40, 100.

Embodiment 4

FIGS. 7A and 7B illustrate a balloon inflatable vascular drug delivery system 300. Vascular drug delivery system 300 includes substrate 310 with rotatable lateral struts 312 with projections 316, and inflatable balloon 350, and is suitable for intravascular delivery to a target site within a patient's vasculature. Upon reaching the target site vascular drug delivery system 300 facilitates deployment through remote inflation of balloon 350. Specifically, FIG. 7A illustrates vascular drug delivery system 300 in a deflated configuration, whereas FIG. 7B illustrates vascular drug delivery system 300 in an inflated configuration.

For example, vascular drug delivery system 300 may further include a therapeutic coating 360 including a therapeutic agent covering all or portions of substrate 310, rotatable lateral struts 312 with projections 316, and/or inflatable balloon 350. As described previously, projections extending from rotatable struts, such as projections 316, may include a therapeutic compound, and/or represent microneedles configured to deliver a therapeutic fluid.

Vascular drug delivery system 300 is operable to apply a therapeutic agent, to the surrounding tissue along its length. For example, the therapeutic agent can be intimately applied to at least a majority portion of the surrounding tissue along this length.

In some embodiments, vascular drug delivery system 300 may be configured to displace at least a portion of a fluid, such as blood, along the length of a vessel and thus, substantially occlude the vessel along this length. In effect, the close proximity to the surrounding tissue and the displacement of blood can reduce the amount of therapeutic agent required for an effective treatment as well as the amount of therapeutic agent migrating away from the treatment site.

Substrate 310 defines a tubular major surface 309 including circumferential struts 314 and rotatable lateral struts 312 with projections 316 extending from intermediate sections 315 of the lateral struts 312. Substrate 310 is configured such that when substrate 310 is stretched in a circumferential direction through the inflation of balloon 350, the lateral struts 312 rotate relative to the circumferential struts 314 and bend out of plane of the major surface 309 such that the barbed projections 316 rotate relative to the circumferential struts 314. Major surface 309 forms a tubular shape, the original plane of tubular major surface 309 is also tubular. Geometrically, bending out of the plane of the major surface 309 may represent bending either inwardly and/or outwardly in a radial dimension.

The plane of a tubular major surface is a plane defined wherein a tubular substrate is longitudinally cut and laid open flat about a plane. In a tubular arrangement, the plane defined by a tangent to the tubular substrate major surface to describe the projections moving out of the local plane inwardly and/or outwardly in a radial dimension.

In the deflated configuration of FIG. 7A, projections 316 are along the major surface 309 of the lateral struts 312 and the circumferential struts 314. In the inflated configuration of FIG. 7B, lateral struts 312 with projections 316 are rotated to point outward from the major surface 309 of circumferential struts 314 and from the original plane of tubular major surface 309.

The tubular major surface 309 of substrate 310, including circumferential struts 314 and lateral struts 312, defines a longitudinal axis 330. Projections 316 extend about perpendicular to longitudinal axis 330 in both the stretched and unstretched configurations. As represented in FIG. 7B, projections 316 extend radially outward when substrate 310 is radially stretched due to the rotation of the intermediate sections 315 of the lateral struts 312. The projections 316 may remain coincident relative to the tubular substrate 310 when the tubular substrate 310 is radially unstretched, and the projections 316 may extend radially outward when radial stretching of the substrate induces rotation of lateral struts 312 relative to the circumferential struts 314.

In a modified embodiment, a tubular substrate may include rotatable circumferential struts which rotate in response to longitudinal stretching of the substrate. In such an embodiment, projections remain flat relative to the substrate when the substrate is longitudinally stretched and radially unstretched, and the projections may extend radially outward when longitudinal stretching of the substrate induces rotation of the circumferential struts relative to the lateral struts.

In various embodiments, the tubular substrate 310 may be radially self-expandable. In such embodiment, tubular substrate 310 may be constrained within an elongated tubular catheter prior to expansion, and balloon 350 may be optional. Alternatively, following expansion of tubular substrate 310 to an intermediate diameter, balloon 350 may be used to further radially expand tubular substrate 310 to an expanded diameter, for example, to drive barbed projections 316 into a patient tissue or other material.

For example, tubular substrate 310 may be radially self-expandable from a collapsed diameter within an elongated tubular catheter to an intermediate diameter and radially balloon-expandable to an expanded diameter from the intermediate diameter. In some of such embodiments, the intermediate sections 315 of the lateral struts 312 rotate relative to the circumferential struts 314 between the collapsed diameter and the expanded diameter. In some of such embodiments, the intermediate sections 315 of the lateral struts 312 may not significantly rotate relative to the circumferential struts 314 between the collapsed diameter and the intermediate diameter during the self-expansion, but instead mostly rotate between the intermediate diameter and the expanded diameter during the balloon-expansion.

Substrate 310 is similar to substrates 10, 40, 100, 200 and substrates 10, 40, 100, 200 may be combined with elements and features with respect to system 300 by modifying or replacing substrate 310 with any of the features or elements described with respect to substrates 10, 40, 100, 200.

In embodiments in which projections 316 represent microspikes (with or without central apertures), covered with a therapeutic material, and stretching of substrate 310 fractures the therapeutic coating to facilitate delivery of the therapeutic coating to a patient tissue adjacent the therapeutic coating. The microspikes may be used to create drug depot locations in a vessel wall, such as an artery wall. Such techniques may not only provide relatively high percentage drug tissue concentrations, but locations where the depots gets lodged (to prevent simply having the drug particles being washed downstream after balloon treatment). In such embodiments, microspike projections 316 become exposed during balloon inflation to help disrupt the internal elastic lamina layer of a vasculature. The microspike projections 316 are retracted prior to inflation and may also be protected during delivery to the target site. In some embodiments, the therapeutic material 360 may contain a combination of solubilized formulation of a therapeutic compound along with slow-dissolving paclitaxel crystals.

In some embodiments, balloon 350 may be covered with the therapeutic material 360 and microspike projections 316 may function to radially align crystals to be directed into the internal elastic lamina layer of a vasculature, rather than simply press up against the internal elastic lamina layer of a vasculature during inflation of a similar system without substrate 310. Microspike projections 316 in the deployed state (FIG. 7B) break-up therapeutic material 360 and can create a higher proportion of vertically oriented drug formulation particles and resulting drug retention into the artery wall after inflation and deflation. In contrast a similar system without substrate 310 may simply push flat formulation pieces (most in-plane to the balloon surface and to the vessel luminal wall) towards the wall with little mechanism for formulation adhesion to the wall after the balloon is deflated and vessel blood flow is restored. Thus, the inclusion of substrate 310 with microspike projections within a drug delivery system may result in improved drug delivery efficiency, and a reduction in drug amount delivered to patient blood.

Generally it may be preferable for microspike projections 316 to retract upon balloon deflation, such that the material of substrate 310 should be of sufficient elasticity to collapse upon balloon deflation. Such materials may include nitinol, or other metals.

In some embodiments, microspike projections 316 may extend between 200 and 1000 micrometers, such as about 500 micrometers. Such lengths may allow drug formulation to penetrate from the endothelium thru the media toward the adventitia, which is the targeted area and site of greatest drug retention. This may allow drug delivery thru the fibrous cap on arterial wall plaque segments.

In the same or different embodiments, vascular drug delivery system 300 may include from about 25 to about 50 microspike projections 316 for a balloon size of 5 millimeters diameter by about 40 millimeters long. These dimensions and number of microspike projections 316 are merely examples, and other dimensions and number of projections may be selected for various applications.

In the same or different embodiments, microspike projections 316 may deploy upon balloon inflation to about half of the final diameter. Such a configuration may radially align fragments for delivery to variety of vessel diameters ranging from about half of the final diameter to the final diameter.

Balloon 350 may be selected according to the design requirements of the particular application, including the resistance to deployment provided by substrate 310 and therapeutic material 360, as well as a desired range of radial force to be applied to a vessel wall during deployment to improve delivery of the therapeutic material 360 without causing undesirable damage to the vessel wall.

For example, balloon formation can be carried out in any conventional manner using known extrusion, blow molding and other molding techniques. Typically, three major steps in the process include extruding a tubular preform, molding the balloon and annealing the balloon. Depending on the balloon material employed, the preform can be axially stretched before it is blown.

The balloon can be attached to an elongate member (not shown) to facilitate delivery within a vasculature by various bonding techniques known to the skilled artisan. Embodiments include, but are not limited to, solvent bonding, thermal adhesive bonding and heat shrinking or sealing. The selection of the bonding technique is dependent upon the materials from which the expandable element and tubular body are prepared.

According to the present disclosure, the balloon can be formed using any materials known to those of skill in the art with the desired physical properties. Commonly employed materials include the thermoplastic elastomeric and non-elastomeric polymers and the thermosets.

In an example system 300, the collapsed diameter of 6 French allowed for a 5 millimeter deployed diameter with a 40 millimeter balloon length, representing a 250 percent balloon expansion. This example may be adjusted to correspond to other vessel sizes, including, but not limited to, 4-8 millimeter diameters, 40-200 millimeter lengths, 6 French introducer sheath size, or 7 French introducer sheath size for delivery of balloons with 7 or 8 millimeter deployed diameters.

In below the knee applications: 2.0-4.0 millimeter diameters, 40-200 millimeter lengths, and 4-5 French introducer profile may be utilized.

In any of these examples, the formulation of therapeutic material 360 may be somewhat brittle to facilitate break up and release from microspike projections 316 and balloon 350 when deployed.

System 300 facilitates a variety of coating options. As one example, therapeutic material 360 may be over balloon 350, but under substrate 310. Such an embodiment allows microspike projections 316 to deploy without interference from therapeutic material 360. Also, with this embodiment, substrate 310 protects therapeutic material 360 during tracking and primary lesion. In variations of this embodiment, balloon 350 may be dip coated before loading substrate 310 on balloon 350.

In another example, therapeutic material 360 may be over balloon 350, and substrate 310, as shown in FIG. 7A. In such an example, deployment allows microspike projections 316 to force the breakup of therapeutic material 360. In variations of this embodiment, all of substrate 310 and balloon may be dip coated after loading substrate 310 on balloon 350.

In another example, therapeutic material 360 may be only coated on all or a portion of substrate 310, such as coated on microspike projections 316. Such an example would allow therapeutic material 360 to penetrate the vessel wall. This example, may result in the highest proportion of therapeutic material 360 being delivered to the vessel wall. In variations of this embodiment, all of substrate 310 may be dip coated before loading on balloon 350.

Embodiments in which balloon 350 is covered with therapeutic material 360 and the microneedles of projections 316 function to radially align crystals to be directed into the internal elastic lamina layer of a vasculature, may provide one or more advantages as compared to a similar drug delivery system without substrate 310. For example, the applied techniques may provide enhanced patient safety due to: a reduction in paclitaxel drug content/device, a reduced procedure time due to no requirement for a pre-dilatation balloon inflation prior to deployment (primary angioplasty ability), a reduced inflation time, a reduction in particles delivered distally via blood stream, and a reduced occurrence of segment drug overdosing, a reduction in vessel dissections and reduction in vessel recoil needing stenting due to forced concentric dilatation of vessel during angioplasty, enhanced clinical outcomes as a result of increased improvement in drug uptake consistency, and improvement in drug delivery efficiency, a reduced occurrence of segment drug underdosing, and/or forced concentric inflation from substrate 310, resulting in reduced vessel dissections and vessel recoil. Microspike projections 316 may also protect a drug formulation during introducer valve crossing and tracking to treatment site, which may mitigate loss of formulation in tortuous arteries prior to inflation and may enable primary angioplasty. Such advantages may provide outcomes result in a greater treatment success, more consistent patient success and across a larger patient group (i.e., reduced number of clinical "non-responders") compared to similar drug delivery system without substrate 310.

Embodiment 5

FIGS. 8A-8C illustrate deployment of barbed sleeves from projections to secure two tissue layers together. Specifically, FIG. 8A illustrates vessel 460 with tissue layers 462, 464 separated from one another. As an example, FIG. 8A may represent a vessel dissection, with the tissue layer 462 being a vessel wall and the tissue layer 464 being an intimal flap.

FIG. 8B illustrates a balloon inflatable vascular delivery system 400. The vascular delivery system 400 includes substrate 410 with rotatable lateral struts 412 with projections 416, circumferential struts (not shown in FIG. 8B) and inflatable balloon 450, and is suitable for intravascular delivery to a target site within a patient's vasculature via elongated member 440. The vascular delivery system 400 may further include a delivery device (not shown). Upon reaching the target site, the vascular drug delivery system 400 facilitates deployment through remote inflation of the balloon 450.

The vascular delivery system 400 and its variations are the same or similar to those described with respect to the vascular delivery system 300, with the exception of the addition of caps 420 over the distal ends of the projections 416. In some embodiments, the caps 420 may represent coating or releasable sheaths on the projections 416.

Since the projections 416 lay flat against the balloon 450 in the un-deployed state, the caps 420 are deployable within a patient's vasculature with vascular delivery system 400. Upon arrival at the target therapy site, the balloon 450 may be remotely inflated and the projections 416 will rotate into place during deployment, as described previously, e.g., with respect to delivery system 300. Inflation of the balloon 450 may be the cause the projections 416 and the caps 420 to embed into the vessel wall, including the tissue layers 462, 464, as shown in FIG. 8B. In the specific embodiment shown, caps 420 may represent a barbed sleeve, suitable for tacking tissue layers 462, 464 together, for example, to repair an intimal flap. As shown in the enlarged portion of FIG. 4B, a cap 420 includes a pointed tip 422 and barbs 426 on the walls of cap 420. In the same or different embodiment, caps 420 may include drugs that can be driven into a vessel wall and left behind following the removal or retraction of the projections 416.

As shown in FIG. 8C, vascular delivery system 400 has been withdrawn from the vessel, leaving caps 420 behind. In this specific embodiment, the intimal flap has been repaired as caps 420 function to secure tissue layer 464 to tissue layer 462.

The caps 420 may also be used to deliver a therapeutic agent to the vessel wall. The caps 420 may be permanent or bio-absorbable. The caps 420 may be textured or barbed as to lock into the tissue. For example, the caps 420 themselves may comprise barbs which assist in anchoring the sheath in place. The caps 420 may be polymeric or metallic. The caps 420 may comprise swellable portions. For instance, tips of caps 420 may be coated in a hydrogel which swells as it absorbs moisture. This swelling tip may help to anchor the caps 420 in place.

Substrate 410 is similar to substrates 10, 40, 100, 200, 310 and substrates 10, 40, 100, 200, 310 may be combined with elements and features with respect to system 400 by modifying or replacing substrate 410 with any of the features or elements described with respect to substrates 10, 40, 100, 200, 310.

Embodiment 6

FIGS. 9A-9D illustrate a medical device 500 suitable for endoluminal delivery. Medical device 500 includes a diametrically adjustable tubular substrate 510 with substrate 560 defining rotatable lateral struts 512 with raised edges 515 and circumferential struts 514 mounted on elongated member 540. Raised edges 515 are suitable for removing thrombus from a vasculature, as described with respect to FIGS. 10A-10C.

Substrate 510 defines a tubular major surface 509 including circumferential struts 514 and rotatable lateral struts 512. Substrate 510 is configured such that when substrate 510 is stretched in a circumferential direction through the inflation of balloon 550, the lateral struts 512 rotate relative to the circumferential struts 514 and bend out of plane of the major surface 509 such that the raised edges 515 extend radially outward.

Medical device 500 may be part of a vascular delivery system suitable for intravascular delivery to a target site within a patient's vasculature via elongated member 540. The vascular delivery system may further include an inflatable balloon and/or a delivery device (not shown). Such a vascular delivery system and its variations are the same or similar to those described with respect to the vascular delivery system 300, with the exception of the absence of projections from the lateral struts 512. For example, upon arrival at a target therapy site, the balloon may be remotely inflated and the lateral struts 512 will rotate into place during deployment, as described previously, e.g., with respect to delivery system 300.

Substrate 510 is similar to substrates 10, 40, 100, 200, 310, 410 and substrates 10, 40, 100, 200, 310, 410 may be combined with elements and features with respect to medical device 500 by modifying or replacing substrate 510 with any of the features or elements described with respect to substrates 10, 40, 100, 200, 310, 410.

Figure 10A:
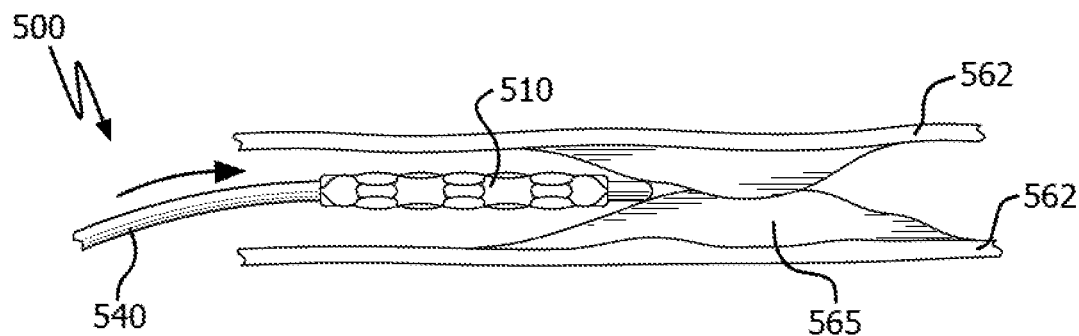
FIGS. 10A-10C illustrate removing a thrombus from a vasculature of a patient using the medical device of FIGS. 9A-9D, in accordance with an embodiment.
Figure 10B:
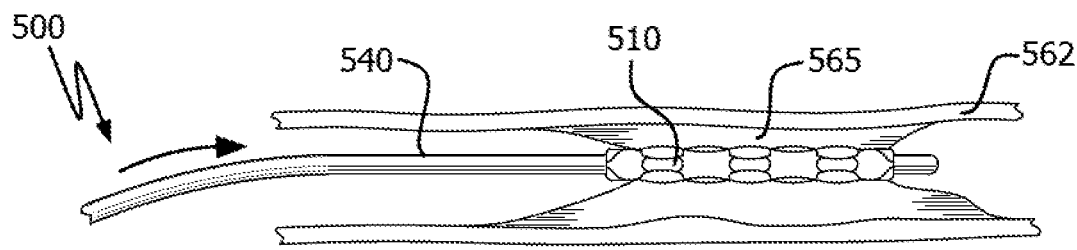
Figure 10C:
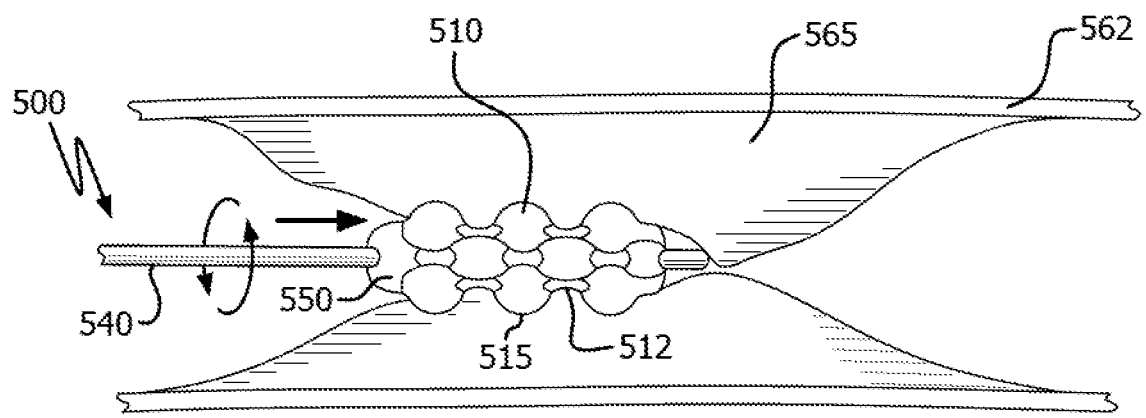

FIGS. 10A-10C illustrate removing a thrombus 565 from a vasculature 562 of a patient using the medical device 500. The thrombus 565 is a vessel occlusion, which may substantially prevent blood flow through the vasculature 562. The medical device 500 may be used to scrape and clear the thrombus 565 as shown. First, the medical device 500 is delivered to the target therapy site, i.e., the location of thrombus 565 in the vasculature 562 (FIG. 10A). Then, the distal end of the medical device 500, including the substrate 510 is pushed into the thrombus 565 (FIG. 10B). Next, the substrate 510 is expanded, for example, with a balloon (not shown) to rotate the lateral struts 512 and expose the raised edges 515. The exposed raised edges 515 are then used to scrape and clear the thrombus 565 by rotating the substrate 510 and or moving the substrate longitudinally within the vasculature 562, for example, via remote operation of elongated member 540 (FIG. 10C). The raised edges 515 of the lateral struts 512 may act as a scoop to remove the thrombus 565 from the walls of the vasculature 562. A bag or other filter (not shown) may be used to capture released dislodged thrombotic particles downstream within the vasculature 562. The same or similar techniques may be used to remove plaque from within the vasculature 562.

Embodiment 7

In some embodiments, and referring to FIG. 7B, the tubular substrate 310 could be suitable for intravascular delivery to a target site within a patient's vasculature.

The tubular substrate 310 could be deployed by balloon (not shown), until the projections 316 reach and pierce the vessel. In this embodiment, projections 316 would be configured with texture or barbs to enable them to engage and grip tissue, such as those illustrated in FIG. 4B, FIG. 4C, FIG. 4D and FIG. 4G. Upon balloon deflation, projections 316 with barbs will pull the vessel or host tissue down with it. In this instance, the tubular substrate 310 may be left in the vessel and act to reduce the vessel diameter.

Such techniques may be applied to standardize the ostium of the left atrial appendage, to restore competency to a venous valve, to build a landing zone for an abdominal aneurysm stent-graft just below the renal arteries, and/or to completely close a vessel (fully occlude). In some of such embodiments, the tubular substrate 310 may operate as "reverse" stent. In some of such embodiments, tubular substrate 310 may be formed from a shape memory alloy heat set in a collapsed diameter. In such embodiments, projections 316 may be heat set outward or heat set to rotate outward with rotatable lateral struts 312 during the expansion of tubular substrate 310 from a collapsed diameter to an expanded diameter.

In some of such embodiments, the projections 316 may be constrained by the delivery catheter device prior to deployment of the tubular substrate 310 from the distal end of the delivery catheter device.

In the same or different embodiments, the tubular substrate 310 may be mounted on a balloon to facilitate radial expansion of the tubular substrate 310 and/or penetration of the projections 316 within a patient tissue or graft material. Inflating the balloon will drive the barbs into the tissue or graft material. Deflating the balloon will allow the tubular substrate 310 to draw the orifice closed.

At the entrance of the left atrial appendage, the sheath would be pulled back, deploying the projections 316, which serve as anchors. Inflating the balloon will drive the barbs into the tissue. Deflating the balloon will allow the stent to draw the orifice closed tubular substrate 310 to draw the orifice closed. In this manner, the stent is configured to radially collapse to draw together tissue surfaces captured by the plurality of projections.

While this technique is described with respect to cause occlusion of the ostium of a left atrial appendage of a patient, it may be radially applied to draw together other tissues. For example, tubular substrate 310 may be deployed to cause occlusion of a blood vessel, to cause occlusion of a tubular conduit or organ, to facilitate closure of a wall defect, to facilitate closure of a topical wound, to facilitate closure of an internal wound, or to facilitate occlusion of closure of an orifice or void within a patient.

In the same or different embodiments, a medical device including the tubular substrate 310 may further include a collar configured to substantially cover a central lumen of the tubular substrate 310. Optionally, such a collar could then be slid onto tubular substrate 310, closing the orifice completely. The tabs opposite the projections 316 could be used to trap the collar. If desired for further fixation, a Septal defect closure device (such as Gore Helex or Eclipse) could be deployed through the central lumen of tubular substrate 310.

Tubular substrate 310 may be combined with other techniques for occluding a left atrial appendage of a patient, for example, as described in U.S. Pat. No. 9,186,152, titled LEFT ATRIAL APPENDAGE OCCLUSIVE DEVICES, which is incorporated by reference herein for all purposes.

Embodiment 8

A medical system may include a medical device with a tubular substrate corresponding to one of the substrates 10, 40, 100, 200, 310, 410, or 510, and a delivery device configured to deliver the medical device within a vasculature of a patient with the medical device in a collapsed configuration. The delivery device is operable to deploy the tubular substrate within the vasculature. Deployment of the medical device includes stretching of the tubular substrate to an expanded configuration such that the lateral struts are configured to rotate relative to the longitudinal struts. The tubular substrate is configured to engage an inner wall of the vasculature.

In some of such embodiments, the deployment of the medical device includes stretching of the tubular substrate to the expanded configuration such that the lateral struts and the projections are configured to rotate relative to the longitudinal struts. The projections may be configured to penetrate an inner wall of the vasculature.

In the same or different embodiments, the tubular substrate forms at least a portion of a stent. For example, the projections may function as tissue engagement members of stent or stent graft as described in U.S. Pat. No. 9,333,101, titled MEDICAL DEVICE FIXATION ANCHORS, which is incorporated by reference herein for all purposes.

In some of such embodiments in which the tubular substrate forms at least a portion of a stent, the medical device may further comprise a tubular graft layered with the substrate to form a stent graft.

Embodiment 9 (Valve Embodiment)

A medical system may include a medical device with a tubular substrate corresponding to one of the substrates 10, 40, 100, 200, 310, 410, or 510, and a delivery device configured to deliver the medical device within a vasculature of a patient with the medical device in a collapsed configuration. The delivery device is operable to deploy the tubular substrate within the vasculature. Deployment of the medical device includes stretching of the tubular substrate to an expanded configuration such that the lateral struts are configured to rotate relative to the longitudinal struts.

The substrate of the medical device includes projections operable to penetrate at least one of tissue of a patient and graft material of an implantable medical device, such a graft material of a heart valve device as part of a valve-in-a-valve implantation procedure.

Embodiment 10

A medical system may include a medical device with a substrate corresponding to one of the substrates 10, 40, 100, 200, 310, 410, or 510, and a delivery device configured to deliver the medical device within a confined orifice of a patient. The substrate is a flat sheet curled up within the delivery device. The delivery device is operable to deploy the substrate within the confined orifice such that the flat sheet at least partially uncurls within the confined orifice.

Deployment of the medical device may include stretching of the substrate to an expanded configuration such that the lateral struts are configured to rotate relative to the longitudinal struts.

In some of such embodiments, the medical device is configured to be used as a hernia patch with the projections being configured to contact or penetrate a patient tissue following deployment of the substrate from the delivery device. In such embodiments, projections may be configured to contact or penetrate a tissue of the patient adjacent an opening in the tissue at a herniation. For example, the substrate may function as a hernia patch as described in United States Patent Application Publication No. 2012/0065649, titled SURGICAL MESH, which is incorporated by reference herein for all purposes.

Some representative embodiments of this disclosure may be characterized according to the following clauses.

Clause 1: A medical device comprising: a substrate defining a major surface, the major surface defining a plane, the major surface including a plurality of first struts extending along a first direction that are interconnected with a plurality of second struts extending along a second direction not parallel with the first direction along the major surface, wherein widths of the second struts as measured along the major surface are larger than thicknesses of the second struts as measured perpendicular to the major surface such that when the substrate is stretched in the first direction, intermediate sections of the second struts rotate relative to the first struts and the intermediate sections of the second struts bend out of the plane of the major surface.

Clause 2: The medical device of clause 1, wherein the first direction is perpendicular to the second direction.

Clause 3: The medical device of clause 1 or clause 2, wherein the plurality of second struts alternately extend at an angle to a transverse direction defining a serpentine portion with peaks and valleys with the plurality of first struts interconnecting the plurality of second struts adjacent apexes of the peaks and valleys.

Clause 4: The medical device of clause 3, wherein the serpentine portion include V-shaped portions including the peaks and valleys.

Clause 5: The medical device of clause 3, wherein the serpentine portion include U-shaped portions including the peaks and valleys.

Clause 6. The medical device of any of clauses 1-5, wherein the plurality of first struts have a curved shape operable to allow expansion of the first struts along the first direction prior to the rotation of the intermediate sections of the second struts as the substrate is stretched along the direction perpendicular to the first direction.

Clause 7: The medical device of any of clauses 1-6, wherein the substrate comprises one or more of: metal, plastic, superelastic metals, and shape memory materials.

Clause 8: The medical device of any of clauses 1-7, wherein the substrate includes nitinol operable to self-expand to elongate the substrate along the direction perpendicular to the first direction or self-contract to retract the substrate along the direction perpendicular to the first direction.

Clause 9: The medical device of any of clauses 1-8, wherein the stretching of the substrate along the direction perpendicular to the first direction results in plastic deformation of the substrate.

Clause 10: The medical device of any of clauses 1-8, wherein the stretching of the substrate along the direction perpendicular to the first direction results in elastic deformation of the substrate.

Clause 11: The medical device of any of clauses 1-10, wherein the substrate is flat.

Clause 12: The medical device of any of clauses 1-10, wherein the substrate is a tubular substrate.

Clause 13: The medical device of clause 12, wherein the tubular substrate is radially self-expandable.

Clause 14: The medical device of clause 12 or clause 13, wherein the tubular substrate is radially balloon-expandable.

Clause 15: The medical device of clause 14, wherein the tubular substrate is radially self-expandable to an intermediate diameter from a collapsed diameter, wherein the tubular substrate is radially balloon-expandable to an expanded diameter from the intermediate diameter, and wherein the intermediate sections of the second struts rotate relative to the first struts between the collapsed diameter and the expanded diameter.

Clause 16: The medical device of clause 15, wherein the intermediate sections of the second struts rotate relative to the first struts between the intermediate diameter and the expanded diameter, and wherein the intermediate sections of the second struts do not significantly rotate relative to the first struts between the collapsed diameter and the intermediate diameter.

Clause 17: The medical device of any of clauses 1-16, further comprising a therapeutic coating covering at least a portion of the substrate, wherein the rotation of the intermediate sections from the stretching of the substrate along the direction perpendicular to the first direction fractures the therapeutic coating to facilitate delivery of the therapeutic coating to a patient tissue adjacent the therapeutic coating.

Clause 18: The medical device of any of clauses 1-17, further comprising a plurality of projections extending from the intermediate sections of the plurality of second struts, wherein, when the substrate is stretched along the direction perpendicular to the first direction, the plurality of projections rotate with the intermediate sections of the plurality of second struts to project outwardly relative to the plurality of first struts.

Clause 19: The medical device of clause 18, further comprising caps over distal ends of each of the plurality of projections, the caps being configured to remain within a patient tissue following insertion and removal of the distal ends into the patient tissue.

Clause 20: The medical device of clause 18, wherein the plurality of projections each extend within the substrate parallel to the first struts.

Clause 21: The medical device of any of clauses 18-20, wherein the plurality of projections extend from opposing sides of the plurality of second struts such that when the substrate is stretched along the direction perpendicular to the first direction, the plurality of projections rotate with the intermediate sections of the plurality of second struts to project in opposing directions relative to the plurality of first struts.

Clause 22: The medical device of any of clauses 18-21, wherein the plurality of projections define anchors, each anchor including a pointed tip.

Clause 23: The medical device of clause 22, wherein the anchors are operable to penetrate at least one of tissue of a patient and graft material of an implantable medical device.

Clause 24: The medical device of clause 22 or clause 23, wherein the anchors each include a base portion, a tip end portion distal to the base portion, and a body portion between the base portion and the tip end portion, wherein the base portion is integral with one of the intermediate sections of the plurality of second struts.

Clause 25: The medical device of clause 24, wherein the anchors are operable to penetrate tissue of a vessel and wherein the tip end portion is operable to prevent pullout once penetrated into tissue.

Clause 26: The medical device of clause 24 or clause 25, wherein a form of the tip end portion is selected from a group consisting of: pointed, arrowhead, single sided arrowhead, barbed, textured, rectangular, square, oval, circular, diamond, triangular, elliptical, polygonal, U-shaped, and star-shaped.

Clause 27: The medical device of any of clauses 22-26, wherein the anchors are operable to perform one of more of: anchor into tissue, deliver drugs to tissue, stimulate tissue, conceal tissue, expose tissue, secure tissues together, and secure tissue to a medical device.

Clause 28: The medical device of any of clauses 22-27, wherein the anchors each include a removable distal section.

Clause 29: The medical device of clause 28, wherein the removable distal section includes one or more of: a barbed sleeve, an erodible portion, an absorbable portion, a break-off distal portion, a tacky distal portion, a barbed, break-off distal tip, a therapeutic compound, and biological moieties.

Clause 30: The medical device of any of clauses 18-21, wherein the plurality of projections are microneedles including lumens in fluid communication with a manifold and a fluid repository, and wherein the microneedle are operable to deliver a therapeutic fluid or collect a sample via the lumens and the manifold.

Clause 31: The medical device of clause 30, wherein at least some of the first and second struts are of tubular construction and having lumens and in fluid communication with the microneedles and the fluid repository.

Clause 32: The medical device of clause 30 or clause 31, wherein the fluid repository is located adjacent a proximal end of a delivery device suitable to facilitate delivery of the medical device.

Clause 33: The medical device of clause 30 or clause 31, wherein the fluid repository is located adjacent a proximal end of the medical device.

Clause 34: The medical device of any of clauses 18-33, further comprising a therapeutic coating covering the plurality of projections, wherein the rotation of the plurality of projections from the stretching of the substrate along the direction perpendicular to the first direction fractures the therapeutic coating to facilitate delivery of the therapeutic coating to a patient tissue adjacent the therapeutic coating.

Clause 35: The medical device of any of clauses 18-34, wherein the substrate is a tubular substrate, wherein the tubular substrate defines a lumen having a longitudinal axis, wherein the plurality of projections remain coincident relative to the substrate when the substrate is radially unstretched, and wherein the plurality of projections extend radially outward when radial stretching of the substrate induces rotation of the second struts relative to the first struts.

Clause 36: The medical device of clause 35, wherein the plurality of projections remain flat relative to the substrate when the substrate is longitudinally stretched and radially unstretched.

Clause 37: The medical device of any of clauses 18-34, wherein the substrate is a tubular substrate, wherein the tubular substrate defines a lumen having a longitudinal axis, wherein the plurality of projections remain coincident relative to the substrate when the substrate is longitudinally unstretched, and wherein the plurality of projections extend radially outward when longitudinal stretching of the substrate induces rotation of the second struts relative to the first struts.

Clause 38: The medical device of clause 37, wherein the plurality of projections remain flat relative to the substrate when the substrate is radially stretched and longitudinally unstretched.

Clause 39: The medical device of any of clauses 35-38, wherein the medical device is configured to radially collapse to draw together tissue surfaces captured by the plurality of projections.

Clause 40: The medical device of clause 39, wherein the medical device further includes a collar configured to substantially cover the lumen.

Clause 41: The medical device of any of clauses 35-40, wherein the tubular substrate is radially self-expandable.

Clause 42: The medical device of clause 41, wherein the tubular substrate is radially balloon-expandable.

Clause 43: The medical device of clause 42, wherein the tubular substrate is radially self-expandable to an intermediate diameter from a collapsed diameter, wherein the tubular substrate is radially balloon-expandable to an expanded diameter from the intermediate diameter, and wherein the plurality of projections rotate with the intermediate sections of the plurality of second struts to project outwardly relative to the plurality of first struts between the collapsed diameter and the expanded diameter.

Clause 44: The medical device of clause 43, wherein the plurality of projections rotate with the intermediate sections of the plurality of second struts to project outwardly relative to the plurality of first struts between the intermediate diameter and the expanded diameter, and wherein the plurality of projections remain flat relative to the substrate when the substrate expands from the collapsed diameter to the intermediate diameter.

Clause 45: The medical device of any of clauses 12-17 and 35-44, wherein the tubular substrate forms at least a portion of a stent.

Clause 46: The medical device of clause 45, further comprising a tubular graft layered with the substrate to form a stent graft.

Clause 47: A medical system comprising: the medical device of any of clauses 1-46, and a delivery device configured to induce the stretching of the substrate, wherein a deployment of the medical device includes stretching of the substrate such that the second struts rotate relative to the first struts.

Clause 48: A medical system comprising: the medical device of any of clauses 18-34, and a delivery device configured to deliver the medical device within a confined orifice of a patient, wherein the substrate is a flat sheet curled up within the delivery device, wherein the delivery device is operable to deploy the substrate within the confined orifice such that the flat sheet at least partially uncurls within the confined orifice, and wherein the medical device is configured to be used as a hernia patch with the plurality of projections being configured to contact or penetrate a tissue of the patient adjacent an opening in the tissue at a herniation.

Clause 49: A medical system comprising: the medical device of any of clauses 12-17 and 35-46, and a delivery device configured to deliver the medical device within a vasculature of a patient with the medical device in a collapsed configuration, wherein the delivery device is operable to deploy the tubular substrate within the vasculature, and wherein a deployment of the medical device includes stretching of the tubular substrate to an expanded configuration such that the second struts rotate relative to the first struts.

Clause 50: The medical system of clause 49, wherein, when the tubular substrate is deployed in the expanded configuration, raised edges of the tubular substrate are configured to scrape and clear thrombus from within the vasculature.

Clause 51: The medical system of clause 49, wherein, when the tubular substrate is deployed in the expanded configuration, the tubular substrate is configured to engage an inner wall of the vasculature.

Clause 52: A medical system of clause 49, wherein the medical device is the medical device of any of clauses 35-46, and wherein a deployment of the medical device includes stretching of the tubular substrate to the expanded configuration such that the second struts and the plurality of projections rotate relative to the first struts.

Clause 53: The medical system of clause 52, wherein the plurality of projections are configured to penetrate an inner wall of the vasculature.

Clause 54: A method of manufacturing the medical device of any of clauses 1-46, the method comprising: cutting a sheet of substrate material to form the substrate including the plurality of first struts and the plurality of second struts, wherein the plurality of first struts are interconnected with the plurality of second struts in the cut sheet of substrate material.

Clause 55: The method of clause 54, wherein the medical device is the medical device of any of clauses 18-46, and wherein cutting the sheet of substrate material to form the substrate further includes forming the plurality of projections extending from the intermediate sections of the second struts.

Clause 56: The method of clause 54 of clause 55, further comprising stretching the substrate along the direction perpendicular to the first direction to rotate the second struts relative to the first struts and bend the intermediate sections of the second struts in the plane parallel to the widths of the second struts as the substrate elongates along the direction perpendicular to the first direction.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is further claimed is:

1. A medical device comprising:
a substrate defining a major surface, the major surface including a plurality of first struts extending along a first longitudinal direction that are interconnected with a plurality of second struts extending along a second direction not parallel with the first longitudinal direction along the major surface,
wherein widths of the second struts as measured along the major surface are larger than thicknesses of the second struts as measured perpendicular to the major surface such that when the substrate is stretched in the first longitudinal direction, intermediate sections of the second struts rotate relative to the first struts and the intermediate sections of the second struts bend away from the major surface.

2. The medical device of claim 1, wherein the first longitudinal direction is perpendicular to the second direction.

3. The medical device of claim 1, wherein the plurality of second struts alternately extend at an angle to a transverse direction defining a serpentine portion with peaks and valleys with the peaks or valleys of the plurality of first struts interconnecting the peaks or valleys of the plurality of second struts at adjacent apexes.

4. The medical device of claim 1, wherein the plurality of first struts have a curved shape operable to allow expansion of the first struts along the first longitudinal direction prior to rotation of the intermediate sections of the second struts as the substrate is stretched along the direction perpendicular to the first longitudinal direction.

5. The medical device of claim 1, wherein the substrate is a tubular substrate.

6. The medical device of claim 5,
wherein the tubular substrate is radially self-expandable to an intermediate diameter from a collapsed diameter,
wherein the tubular substrate is radially balloon-expandable to an expanded diameter from the intermediate diameter, and
wherein the intermediate sections of the second struts rotate relative to the first struts between the collapsed diameter and the expanded diameter.

7. The medical device of claim 5, further comprising a plurality of projections extending from the intermediate sections of the plurality of second struts,
wherein the medical device is configured to radially collapse to draw together tissue surfaces captured by the plurality of projections.

8. The medical device of claim 5, wherein the tubular substrate forms at least a portion of a stent, the medical device further comprising a tubular graft layered with the substrate to form a stent graft.

9. The medical device of claim 1, further comprising a therapeutic coating covering at least a portion of the substrate, wherein rotation of the intermediate sections from the stretching of the substrate along a direction perpendicular to the first longitudinal direction fractures the therapeutic coating to facilitate delivery of the therapeutic coating to a patient tissue adjacent the therapeutic coating.

10. The medical device of claim 1,
further comprising a plurality of projections extending from the intermediate sections of the plurality of second struts,
wherein, when the substrate is stretched along a direction perpendicular to the first longitudinal direction, the plurality of projections rotate with the intermediate sections of the plurality of second struts to project outwardly relative to the plurality of first struts.

11. A medical system comprising:
a medical device including a substrate defining a major surface, the major surface including a plurality of first struts extending along a first longitudinal direction that are interconnected with a plurality of second struts extending along a second direction not parallel with the first longitudinal direction along the major surface, wherein widths of the second struts as measured along the major surface are larger than thicknesses of the second struts as measured perpendicular to the major surface such that when the substrate is stretched in the first longitudinal direction, intermediate sections of the second struts rotate relative to the first struts and the intermediate sections of the second struts bend away from the major surface; and
a delivery device configured to induce the stretching of the substrate,
wherein a deployment of the medical device includes stretching of the substrate such that the second struts rotate relative to the first struts.

12. The medical system of claim 11, further comprising a plurality of projections extending from the intermediate sections of the plurality of second struts, wherein the delivery device is configured to deliver the medical device within a confined orifice of a patient,
wherein the substrate is a flat sheet curled up within the delivery device,
wherein the delivery device is operable to deploy the substrate within the confined orifice such that the flat sheet at least partially uncurls within the confined orifice, and
wherein the medical device is configured to be used as a hernia patch with the plurality of projections being configured to contact or penetrate a tissue of the patient adjacent an opening in the tissue at a herniation.

13. The medical system of claim 11,
wherein the substrate of the medical device is a tubular substrate,
wherein the delivery device is configured to deliver the medical device within a vasculature of a patient with the medical device in a collapsed configuration,
wherein the delivery device is operable to deploy the tubular substrate within the vasculature, and
wherein a deployment of the medical device includes stretching of the tubular substrate to an expanded configuration such that the second struts rotate relative to the first struts.

14. The medical system of claim 13, wherein, when the tubular substrate is deployed in the expanded configuration, raised edges of the tubular substrate are configured to scrape and clear thrombus from within the vasculature.

15. The medical system of claim 13, wherein, when the tubular substrate is deployed in the expanded configuration, the tubular substrate is configured to engage an inner wall of the vasculature.

16. A medical device comprising:
a substrate defining a major surface, the major surface including a plurality of first struts extending along a first longitudinal direction that are interconnected with a plurality of second struts extending along a second direction along the major surface; and
a therapeutic coating covering at least a portion of the substrate,
wherein intermediate sections of the second struts rotate relative to the first struts and the intermediate sections of the second struts bend away from the major surface, and
wherein rotation of the intermediate sections from the stretching of the substrate along the first longitudinal direction fractures the therapeutic coating to facilitate delivery of the therapeutic coating to a patient tissue adjacent the therapeutic coating.

* * * * *